United States Patent [19]
Gelfand et al.

[11] Patent Number: 5,624,833
[45] Date of Patent: Apr. 29, 1997

[54] **PURIFIED THERMOSTABLE NUCLEIC ACID POLYMERASE ENZYME FROM *THERMOTOGA MARITIMA***

[75] Inventors: David H. Gelfand; Frances C. Lawyer, both of Oakland; Susanne Stoffel, El Cerrito, all of Calif.

[73] Assignee: Hoffmann-La Roche Inc., Nutley, N.J.

[21] Appl. No.: 475,231

[22] Filed: Jun. 7, 1995

Related U.S. Application Data

[60] Division of Ser. No. 971,819, Feb. 3, 1993, Pat. No. 5,420,029, which is a continuation-in-part of Ser. No. 567,244, Aug. 13, 1990, Pat. No. 5,374,553, which is a continuation-in-part of Ser. No. 143,441, Jan. 12, 1988, abandoned, which is a continuation-in-part of Ser. No. 63,509, Jun. 17, 1987, Pat. No. 4,889,818, which is a continuation-in-part of Ser. No. 899,241, Aug. 22, 1986, abandoned.

[51] Int. Cl.$^6$ ................................................ C12N 9/12
[52] U.S. Cl. ............................................................ 435/194
[58] Field of Search ............................................ 435/194

[56] References Cited

U.S. PATENT DOCUMENTS 4,889,818  12/1989  Gelfand et al. ................. 435/194
4,965,188  10/1990  Mullis et al. ....................... 435/6

FOREIGN PATENT DOCUMENTS 0359006  3/1990  European Pat. Off. .
8906691  7/1989  WIPO .

OTHER PUBLICATIONS

Simpson et al., 1990, "Purification and Some Properties of a Thermostable DNA Polymerase From a Thermotoga Species" Biochem. Cell Biol. 68:1292–1296.

Simpson et al., 1990, "Purification of a Thermostable DNA Polymerase From a Thermotoga Species" Ann. New York Acad. Sci. 613:426–428.

Lawyer et al., 1989, "Isolation, Characterization, and Expression in *Escherichia coli* of the DNA Polymerase Gene From Thermus Aquaticus" J. Biol. Chem. 264(11):6427–6437.

Matsuzawa et al., 1988, "Purification and Characterization of Aqualysin I (a thermophilic alkaline serine protease) Produced by Thermus Aquaticus YT–1" Eur. J. Biochem. 171:441–447.

Ruttiman et al., 1985, "DNA Polymerases From the Extremely Thermophilic Bacterium Thermus Thermophilus HB–8" Eur. J. Biochem 149:41–46.

Gelfand et al., 1989, "Taq DNA Polymerase" PCR Technology, Principles and Applications for DNA Amplification, Chapter 2, pp. 17–22 (1989), Ed. by H. A. Erlich.

Leavitt and Ito, 1989, "T5 DNA Polymerase: Structural–Functional Relationships to Other DNA Polymerases" Proc. Natl. Acad. Sci. USA 86:4465–4469.

Bernad et al., 1989, "A Conserved 3'–5' Exonuclease Active Site in Prokaryotic and Eukaryotic DNA Polymerases" Cell 59:219–228.

Huber et al., 1986, "Thermotoga Maritima sp. nov. Represents a New Genus of Unique Extremely Thermophilic Eubacteria Growing Up to 90" Chem. Abstracts 105:386 (Abstract No. 38901u).

Chien et al., 1976, "Deoxyribonucleic Acid Polymerase From the Extreme Thermophile Thermus Aquaticus" J. Bacteriology 127(3):1550–1557.

Suggs et al., 1981, "Use of Synthetic Oligonucleotides as Hybridization Probes: Isolation of Cloned cDNA Sequences for Human B2–Microglobulin" Proc. Natl. Acad. Sci. USA 78(11):6613–6617.

Young and Davis, 1983, "Efficient Isolation of Genes by Using Antibody Probes" Proc. Natl. Acad. Sci. USA 80:1194–1198.

Kaledin et al., 1980, "Isolation and Properties of DNA Polymerase From Extremely Thermophilic Bacterium Thermus Aquatics YT1" Biokhimiya 45(4):644–651.

Barany et al., 1991, "The Ligase Chain Reaction in a PCR World" PCR Methods and Applications 1(1):5–16.

Simpson et al., 1990, "Purification and Some Properties of a Thermostable DNA Polymerase From a Thermotoga Species" Biochem. Cell Biol. 68:1292–1296.

Simpson et al., 1990, "Purification of a Thermostable DNA Polymerase From a Thermotoga Species" Ann. New York Acad. Sci. 613:426–428.

*Primary Examiner*—Keith D. Hendricks
*Attorney, Agent, or Firm*—George W. Johnston; Patricia S. Rocha-Tramaloni; Stacey R. Sias

[57] ABSTRACT

A purified thermostable enzyme is derived from the eubacterium *Thermotoga maritima*. The enzyme has a molecular weight as determined by gel electrophoresis of about 97 kilodaltons and DNA polymerase I activity. The enzyme can be produced from native or recombinant host cells and can be used with primers and nucleoside triphosphates in a temperature-cycling chain reaction where at least one nucleic acid sequence is amplified in quantity from an existing sequence.

12 Claims, No Drawings

PURIFIED THERMOSTABLE NUCLEIC ACID POLYMERASE ENZYME FROM *THERMOTOGA MARITIMA*

This application is a divisional of application Ser. No. 07/971,819 filed Feb. 3, 1993, now U.S. Pat. No. 5,420,029, which is a continuation-in-part of Ser. No. 07/567,244, filed Aug. 13, 1990, now U.S. Pat. No. 5,374,553, which is a continuation-in-part of Ser. No. 07/143,441, filed Jan. 12, 1988, now abandoned, which is a continuation-in-part of Ser. No. 07/063,509, filed Jun. 17, 1987, now U.S. Pat. No. 4,889,818, which is a continuation-in-part of Ser. No. 06/899,241, filed Aug. 22, 1986, now abandoned.

TECHNICAL FIELD

The present invention relates to a purified, thermostable DNA polymerase purified from the hyperthermophilic eubacteria *Thermotoga maritima* and means for isolating and producing the enzyme. Thermostable DNA polymerases are useful in many recombinant DNA techniques, especially nucleic acid amplification by the polymerase chain reaction (PCR).

BACKGROUND ART

In Huber et al., 1986, *Arch. Microbiol.* 144: 324–333, the isolation of the bacterium *Thermotoga maritima* is described. *T. maritima* is a eubacterium that is strictly anaerobic, rod-shaped, fermentative, hyperthermophilic, and grows between 55° C. and 90° C., with an optimum growth temperature of about 80° C. This eubacterium has been isolated from geothermally heated sea floors in Italy and the Azores. *T. maritima* cells have a sheath-like structure and monotrichous flagellation. *T. maritima* is classified in the eubacterial kingdom by virtue of having murein and fatty acid-containing lipids, diphtheria-toxin-resistant elongation factor 2, an RNA polymerase subunit pattern, and sensitivity to antibiotics.

Extensive research has been conducted on the isolation of DNA polymerases from mesophilic microorganisms such as *E. coli*. See, for example, Bessman et al., 1957, *J. Biol. Chem.* 223: 171–177, and Buttin and Kornberg, 1966, *J. Biol. Chem.* 241: 5419–5427. Much less investigation has been made on the isolation and purification of DNA polymerases from thermophiles such as *Thermotoga maritima*. In Kaledin et al., 1980, *Biokhymiya* 45: 644–651, a six-step isolation and enrichment procedure for DNA polymerase activity from cells of a *Thermus aquaticus* YT-1 strain is disclosed. These steps involve isolation of crude extract, DEAE-cellulose chromatography, fractionation on hydroxyapatite, fractionation on DEAE-cellulose, and chromatography on single-strand DNA-cellulose. The molecular weight of the purified enzyme is reported by Kaledin et al. as 62,000 daltons per monomeric unit.

A second enrichment scheme for a polymerase from *Thermus aquaticus* is described in Chien et al., 1976, *J. Bacteriol.* 127: 1550–1557. In this process, the crude extract is applied to a DEAE-Sephadex column. The dialyzed pooled fractions are then subjected to treatment on a phosphocellulose column. The pooled fractions are dialyzed, and bovine serum albumin (BSA) is added to prevent loss of polymerase activity. The resulting mixture is loaded on a DNA-cellulose column. The pooled material from the column is dialyzed. The molecular weight of the purified protein is reported to be about 63,000 daltons to 68,000 daltons.

The use of thermostable enzymes, such as those described in Chien et al. and Kaledin et al., to amplify existing nucleic acid sequences in amounts that are large compared to the amount initially present is described in U.S. Pat. Nos. 4,683,195; 4,683,202; and 4,965,188, which describe the PCR process, each of which is incorporated herein by reference. Primers, template, nucleoside triphosphates, the appropriate buffer and reaction conditions, and polymerase are used in the PCR process, which involves denaturation of target DNA, hybridization of primers, and synthesis of complementary strands. The extension product of each primer becomes a template for the production of the desired nucleic acid sequence. The patents disclose that, if the polymerase employed is a thermostable enzyme, then polymerase need not be added after every denaturation step, because heat will not destroy the polymerase activity.

U.S. Pat. No. 4,889,818, European Patent Publication No. 258,017, and PCT Publication No. 89/06691, the disclosures of which are incorporated herein by reference, describe the isolation and recombinant expression of an ~94 kDa thermostable DNA polymerase from *Thermus aquaticus* and the use of that polymerase in PCR. Although *T. aquaticus* DNA polymerase is especially preferred for use in PCR and other recombinant DNA techniques, there remains a need for other thermostable polymerases.

Accordingly, there is a desire in the art to produce a purified, thermostable DNA polymerase that may be used to improve the PCR process described above and to improve the results obtained when using a thermostable DNA polymerase in other recombinant techniques, such as DNA sequencing, nick-translation, and even reverse transcription. The present invention helps meet that need by providing recombinant expression vectors and purification protocols for *Thermotoga maritima* DNA polymerase.

DISCLOSURE OF INVENTION

The present invention provides a purified thermostable DNA polymerase I enzyme that catalyzes combination of nucleoside triphosphates to form a nucleic acid strand complementary to a nucleic acid template strand. The purified enzyme is the DNA polymerase I from *Thermotoga maritima* (Tma) and has a molecular weight of about 97 kilodaltons (kDa) as measured by SDS-PAGE and an inferred molecular weight, from the nucleotide sequence of the Tma DNA polymerase gene, of 102 kDa. This purified material may be used in PCR to produce a given nucleic acid sequence in amounts that are large compared to the amount initially present so that the sequences can be manipulated and/or analyzed easily.

The gene encoding Tma DNA polymerase enzyme from *Thermotoga maritima* has also been identified, cloned, sequenced, and expressed at high level and provides yet another means to prepare the thermostable enzyme of the present invention. In addition to the intact gene and the coding sequence for the Tma enzyme, derivatives of the coding sequence for Tma DNA polymerase are also provided.

The invention also encompasses a stable enzyme composition comprising a purified, thermostable Tma enzyme as described above in a buffer containing one or more non-ionic polymeric detergents.

Finally, the invention provides a method of purification for the thermostable polymerase of the invention. This method involves preparing a crude extract from *Thermotoga maritima* cells, adjusting the ionic strength of the crude extract so that the DNA polymerase dissociates from nucleic acid in the extract, subjecting the extract to hydrophobic interaction chromatography, subjecting the extract to DNA binding protein affinity chromatography, and subjecting the extract to cation or anion exchange or hydroxyapatite chromatography. In a preferred embodiment, these steps are performed sequentially in the order given above. The nucleotide binding protein affinity chromatography step is preferred for separating the DNA polymerase from endonuclease proteins.

MODES FOR CARRYING OUT THE INVENTION

The present invention provides DNA sequences and expression vectors that encode Tma DNA polymerase, purification protocols for Tma DNA polymerase, preparations of purified Tma DNA polymerase, and methods for using Tma DNA polymerase. To facilitate understanding of the invention, a number of terms are defined below.

The terms "cell," "cell line," and "cell culture" are used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences, such as transcription termination sequences. Eucaryotic cells are known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; the relevant DNA can also be integrated into the host chromosome.

The term "gene" refers to a DNA sequence that codes for the expression of a recoverable bioactive polypeptide or precursor. Thus, the Tma DNA polymerase gene includes the promoter and Tma DNA polymerase coding sequence. The polypeptide can be encoded by a full-length coding sequence or by any portion of the coding sequence so long as the desired enzymatic activity is retained.

The term "operably linked" refers to the positioning of the coding sequence such that control sequences will function to drive expression of the encoded protein. Thus, a coding sequence "operably linked" to a control sequence refers to a configuration wherein the coding sequence can be expressed under the direction of the control sequence.

The term "mixture" as it relates to mixtures containing Tma polymerase refers to a collection of materials that includes Tma polymerase but can also include other proteins. If the Tma polymerase is derived from recombinant host cells, the other proteins will ordinarily be those associated with the host. Where the host is bacterial, the contaminating proteins will be bacterial proteins.

The term "non-ionic polymeric detergents" refers to surface-active agents that have no ionic charge and that are characterized, for purposes of this invention, by an ability to stabilize the Tma enzyme at a pH range of from about 3.5 to about 9.5, preferably from 4 to 8.5. Numerous examples of suitable non-ionic polymeric detergents are presented in copending U.S. patent application Ser. No. 387,003, filed Jul. 28, 1989, the disclosure of which is incorporated herein by reference.

The term "oligonucleotide" as used herein is defined as a molecule comprised of two or more deoxyribonucleotides or ribonucleotides, preferably more than three, and usually more than ten. The exact size will depend on many factors, which in turn depend on the ultimate function or use of the oligonucleotide. The oligonucleotide may be derived synthetically or by cloning.

The term "primer" as used herein refers to an oligonucleotide that is capable of acting as a point of initiation of synthesis when placed under conditions in which primer extension is initiated. An oligonucleotide "primer" may occur naturally, as in a purified restriction digest, or be produced synthetically. Synthesis of a primer extension product that is complementary to a nucleic acid strand is initiated in the presence of four different nucleoside triphosphates and the Tma thermostable enzyme in an appropriate buffer at a suitable temperature. A "buffer" includes cofactors (such as divalent metal ions) and salt (to provide the appropriate ionic strength), adjusted to the desired pH. For Tma polymerase, the buffer preferably contains 1 to 3 mM of a magnesium salt, preferably $MgCl_2$, 50 to 200 μM of each nucleoside triphosphate, and 0.2 to 1 μM of each primer, along with 50 mM KCl, 10 mM Tris buffer (pH 8.0–8.4), and 100 μg/ml gelatin (although gelatin is not required and should be avoided in some applications, such as DNA sequencing).

The primer is single-stranded for maximum efficiency in amplification, but may alternatively be double-stranded. If double-stranded, the primer is first treated to separate its strands before being used to prepare extension products. The primer is usually an oligodeoxyribonucleotide. The primer must be sufficiently long to prime the synthesis of extension products in the presence of the polymerase enzyme. The exact length of a primer will depend on many factors, such as source of primer and result desired, and the reaction temperature must be adjusted depending on primer length to ensure proper annealing of primer to template. Depending on the complexity of the target sequence, the oligonucleotide primer typically contains 15 to 35 nucleotides. Short primer molecules generally require cooler temperatures to form sufficiently stable complexes with template.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template/primer complex for synthesis of the extension product of the primer.

The terms "restriction endonucleases" and "restriction enzymes" refer to bacterial enzymes that cut double-stranded DNA at or near a specific nucleotide sequence.

The term "thermostable enzyme" refers to an enzyme which is stable to heat and is heat resistant and catalyzes (facilitates) combination of the nucleotides in the proper manner to form primer extension products that are complementary to a nucleic acid strand. Generally, synthesis of a primer extension product begins at the 3' end of the primer and proceeds towards the 5' end of the template strand until synthesis terminates. A thermostable enzyme must be able to renature and regain activity after brief (i.e., 5 to 30 seconds) exposure to temperatures of 80° C. to 105° C. and must have a temperature optimum of above 60° C.

The Tma thermostable DNA polymerase enzyme of the present invention satisfies the requirements for effective use in the amplification reaction known as the polymerase chain reaction or PCR. The Tma DNA polymerase enzyme does not become irreversibly denatured (inactivated) when subjected to the elevated temperatures for the time necessary to effect denaturation of double-stranded nucleic acids, a key step in the PCR process. Irreversible denaturation of an enzyme for purposes herein refers to permanent and complete loss of enzymatic activity.

The heating conditions necessary to effect nucleic acid denaturation will depend, e.g., on the buffer salt concentration and the composition, length, and amount of the nucleic acids being denatured, but typically the denaturation temperature ranges from about 80° C. to about 105° C. for a few seconds to minutes. Higher temperatures may be required for nucleic acid denaturation as the buffer salt concentration and/or GC composition of the nucleic acid is increased. The Tma enzyme does not become irreversibly denatured upon relatively short exposures to temperatures of about 80° C.–105° C.

The Tma thermostable enzyme has an optimum temperature at which it functions that is higher than about 60° C. Temperatures below 60° C. facilitate hybridization of primer to template, but depending on salt composition and concentration and primer composition and length, hybridization of primer to template can occur at higher temperatures (e.g., 60° C.–80° C.), which may promote specificity of the primer elongation reaction. The higher the temperature optimum for the enzyme, the greater the specificity and/or selectivity of the primer-directed extension process. The Tma enzyme exhibits activity over a broad temperature range from about 45° C. to 90° C.; a preferred optimum temperature is 75° C.–80° C.

The present invention also provides DNA sequences encoding the thermostable DNA polymerase I activity of *Thermotoga maritima*. The amino acid sequence encoded by this sequence has homology to portions of the thermostable DNA polymerases of *Thermus aquaticus* and *Thermus thermophilus*. The complete coding sequence, from the 5'-ATG start codon to the TGA-3' stop codon, of the Tma DNA polymerase gene is depicted below and listed as SEQ ID NO: 1 in the sequence listing section. The sequence is numbered for reference.

```
1    ATGGCGAGAC TATTTCTCTT TGATGGAACT
     GCTCTGGCCT ACAGAGCGTA
51   CTATGCGCTC GATAGATCGC TTTCTACTTC CAC-
     CGGCATT CCCACAAACG
101  CCACATACGG TGTGGCGAGG ATGCTGGTGA
     GATTCATCAA AGACCATATC
151  ATTGTCGGAA AAGACTACGT TGCTGTGGCT
     TTCGACAAAA AAGCTGCCAC
201  CTTCAGACAC AAGCTCCTCG AGACTTACAA
     GGCTCAAAGA CCAAAGACTC
251  CGGATCTCCT GATTCAGCAG CTTCCGTACA
     TAAAGAAGCT GGTCGAAGCC
301  CTTGGAATGA AAGTGCTGGA GGTAGAAGGA
     TACGAAGCGG ACGATATAAT
351  TGCCACTCTG GCTGTGAAGG GGCTTCCGCT
     TTTTGATGAA ATATTCATAG
401  TGACCGGAGA TAAAGACATG CTTCAGCTTG
     TGAACGAAAA GATCAAGGTG
451  TGGCGAATCG TAAAAGGGAT ATCCGATCTG
     GAACTTTACG ATGCGCAGAA
501  GGTGAAGGAA AAATACGGTG TTGAACCCCA
     GCAGATCCCG GATCTTCTGG
551  CTCTAACCGG AGATGAAATA GACAACATCC
     CCGGTGTAAC TGGGATAGGT
601  GAAAAGACTG CTGTTCAGCT TCTAGAGAAG
     TACAAAGACC TCGAAGACAT
651  ACTGAATCAT GTTCGCGAAC TTCCTCAAAA
     GGTGAGAAAA GCCCTGCTTC
701  GAGACAGAGA AAACGCCATT CTCAGCAAAA
     AGCTGGCGAT TCTGGAAACA
751  AACGTTCCCA TTGAAATAAA CTGGGAAGAA
     CTTCGCTACC AGGGCTACGA
801  CAGAGAGAAA CTCTTACCAC TTTTGAAAGA
     ACTGGAATTC GCATCCATCA
851  TGAAGGAACT TCAACTGTAC GAAGAGTCCG
     AACCCGTTGG ATACAGAATA
901  GTGAAAGACC TAGTGGAATT TGAAAAACTC
     ATAGAGAAAC TGAGAGAATC
951  CCCTTCGTTC GCCATAGATC TTGAGACGTC
     TTCCCTCGAT CCTTTCGACT
1001 GCGACATTGT CGGTATCTCT GTGTCTTTCA
     AACCAAAGGA AGCGTACTAC
1051 ATACCACTCC ATCATAGAAA CGCCCAGAAC
     CTGGACGAAA AAGAGGTTCT
1101 GAAAAAGCTC AAAGAAATTC TGGAGGACCC
     CGGAGCAAAG ATCGTTGGTC
1151 AGAATTTGAA ATTCGATTAC AAGGTGTTGA
     TGGTGAAGGG TGTTGAACCT
1201 GTTCCTCCTT ACTTCGACAC GATGATAGCG
     GCTTACCTTC TTGAGCCGAA
1251 CGAAAAGAAG TTCAATCTGG ACGATCTCGC
     ATTGAAATTT CTTGGATACA
1301 AAATGACATC TTACCAAGAG CTCATGTCCT
     TCTCTTTTCC GCTGTTTGGT
1351 TTCAGTTTTG CCGATGTTCC TGTAGAAAAA
     GCAGCGAACT ACTCCTGTGA
1401 AGATGCAGAC ATCACCTACA GACTTTACAA
     GACCCTGAGC TTAAAACTCC
1451 ACGAGGCAGA TCTGGAAAAC GTGTTCTACA
     AGATAGAAAT GCCCCTTGTG
1501 AACGTGCTTG CACGGATGGA ACTGAACGGT
     GTGTATGTGG ACACAGAGTT
1551 CCTGAAGAAA CTCTCAGAAG AGTACGGAAA
     AAAACTCGAA GAACTGGCAG
1601 AGGAAATATA CAGGATAGCT GGAGAGCCGT
     TCAACATAAA CTCACCGAAG
1651 CAGGTTTCAA GGATCCTTTT TGAAAAACTC
     GGCATAAAAC CACGTGGTAA
1701 AACGACGAAA ACGGGAGACT ATTCAACACG
     CATAGAAGTC CTCGAGGAAC
1751 TTGCCGGTGA ACACGAAATC ATTCCTCTGA
     TTCTTGAATA CAGAAAGATA
1801 CAGAAATTGA AATCAACCTA CATAGACGCT
     CTTCCCAAGA TGGTCAACCC
1851 AAAGACCGGA AGGATTCATG CTTCTTTCAA
     TCAAACGGGG ACTGCCACTG
1901 GAAGACTTAG CAGCAGCGAT CCCAATCTTC
     AGAACCTCCC GACGAAAAGT
1951 GAAGAGGGAA AAGAAATCAG GAAAGCGATA
     GTTCCTCAGG ATCCAAACTG
2001 GTGGATCGTC AGTGCCGACT ACTCCCAAAT
     AGAACTGAGG ATCCTCGCCC
2051 ATCTCAGTGG TGATGAGAAT CTTTTGAGGG
     CATTCGAAGA GGGCATCGAC
```

2101 GTCCACACTC TAACAGCTTC CAGAATATTC AACGTGAAAC CCGAAGAAGT
2151 AACCGAAGAA ATGCGCCGCG CTGGTAAAAT GGTTAATTTT TCCATCATAT
2201 ACGGTGTAAC ACCTTACGGT CTGTCTGTGA GGCTTGGAGT ACCTGTGAAA
2251 GAAGCAGAAA AGATGATCGT CAACTACTTC GTCCTCTACC CAAAGGTGCG
2301 CGATTACATT CAGAGGGTCG TATCGGAAGC GAAAGAAAAA GGCTATGTTA
2351 GAACGCTGTT TGGAAGAAAA AGAGACATAC CACAGCTCAT GGCCCGGGAC
2401 AGGAACACAC AGGCTGAAGG AGAACGAATT GCCATAAACA CTCCCATACA
2451 GGGTACAGCA GCGGATATAA TAAAGCTGGC TATGATAGAA ATAGACAGGG
2501 AACTGAAAGA AAGAAAAATG AGATCGAAGA TGATCATACA GGTCCACGAC
2551 GAACTGGTTT TTGAAGTGCC CAATGAGGAA AAGGACGCGC TCGTCGAGCT
2601 GGTGAAAGAC AGAATGACGA ATGTGGTAAA GCTTTCAGTG CCGCTCGAAG
2651 TGGATGTAAC CATCGGCAAA ACATGGTCGT GA

Both the complete coding sequence of the Tma DNA polymerase gene and the encoded amino acid sequence in three letter abbreviation are provided in the Sequence Listing section as SEQ ID NO: 1. For convenience, the amino acid sequence encoded by the Tma DNA polymerase gene sequence is also depicted below in one letter abbreviation from amino-terminus to carboxy-terminus; the sequence is numbered for reference.

```
1   MARLFLFDGT ALAYRAYYAL DRSLSTSTGI PTNATYGVAR MLVRFIKDHI
51  IVGKDYVAVA FDKKAATFRH KLLETYKAQR PKTPDLLIQQ LPYIKKLVEA
101 LGMKVLEVEG YEADDIIATL AVKGLPLFDE IFIVTGDKDM LQLVNEKIKV
151 WRIVKGISDL ELYDAQKVKE KYGVEPQQIP DLLALTGDEI DNIPGVTGIG
201 EKTAVQLLEK YKDLEDILNH VRELPQKVRK ALLRDRENAI LSKKLAILET
251 NVPIEINWEE LRYQGYDREK LLPLLKELEF ASIMKELQLY EESEPVGYRI
301 VKDLVEFEKL IEKLRESPSF AIDLETSSLD PFDCDIVGIS VSFKPKEAYY
351 IPLHHRNAQN LDEKEVLKKL KEILEDPGAK IVGQNLKFDY KVLMVKGVEP
401 VPPYFDTMIA AYLLEPNEKK FNLDDLALKF LGYKMTSYQE LMSFSFPLFG
451 FSFADVPVEK AANYSCEDAD ITYRLYKTLS LKL-HEADLEN VFYKIEMPLV
501 NVLARMELNG VYVDTEFLKK LSEEYGKKLE ELAEEIYRIA GEPFNINSPK
551 QVSRILFEKL GIKPRGKTTK TGDYSTRIEV LEELAGEHEI IPLILEYRKI
601 QKLKSTYIDA LPKMVNPKTG RIHASFNQTG TATGRLSSSD PNLQNLPTKS
651 EEGKEIRKAI VPQDPNWWIV SADYSQIELR ILAHLSGDEN LLRAFEEGID
701 VHTLTASRIF NVKPEEVTEE MRRAGKMVNF SIIYGVTPYG LSVRLGVPVK
751 EAEKMIVNYF VLYPKVRDYI QRVVSEAKEK GYVRTLFGRK RDIPQLMARD
801 RNTQAEGERI AINTPIQGTA ADIIKLAMIE IDRELKERKM RSKMIIQVHD
851 ELVFEVPNEE KDALVELVKD RMTNVVKLSV PLEVDVTIGK TWS
```

The one letter abbreviations for the amino acids are shown below for convenience.

| F | = | Phenylalanine | H | = | Histidine |
|---|---|---|---|---|---|
| L | = | Leucine | Q | = | Glutamine |
| I | = | Isoleucine | N | = | Asparagine |
| M | = | Methionine | K | = | Lysine |
| V | = | Valine | D | = | Aspartic Acid |
| S | = | Serine | E | = | Glutamic Acid |
| P | = | Proline | C | = | Cysteine |
| T | = | Threonine | W | = | Tryptophan |
| A | = | Alanine | R | = | Arginine |
| Y | = | Tyrosine | G | = | Glycine |

The coding sequence for Tma DNA polymerase I was identified by a "degenerate primer" method that has broad utility and is an important aspect of the present invention. In the degenerate primer method, DNA fragments of any thermostable polymerase coding sequence corresponding to conserved domains of known thermostable DNA polymerases can be identified.

In one embodiment of the degenerate primer method, the corresponding conserved domains are from the coding sequences for and amino acid sequences of the thermostable DNA polymerases of Taq, Tma, and Tth. The degenerate primer method was developed by comparing the amino acid sequences of DNA polymerase I proteins from Taq, Tth, T7, and E. coli in which various conserved regions were identified. Primers corresponding to these conserved regions were then designed. As a result of the present invention, Tma sequences can be used to design other degenerate primers. The generic utility of the degenerate primer process is exemplified herein by specific reference to the method as applied to cloning the Tma gene.

To clone the Tma DNA polymerase I gene, the conserved amino acid sequences were converted to all of the possible codons for each of the amino acids. Due to the degenerate nature of the genetic code, a given amino acid may be represented by several different codons. Where more than one base can be present in a codon for a given amino acid, the sequence is said to be degenerate.

The primers were then synthesized as a pool of all of the possible DNA sequences that could code for a given amino acid sequence. The amount of degeneracy of a given primer pool can be determined by multiplying the number of possible nucleotides at each position.

The more degenerate a primer pool, (i.e., the greater the number of individual unique primer DNA sequences within the pool), the greater the probability that one of the unique primer sequences will bind to regions of the target chromosomal DNA other than the one desired—hence, the lesser the specificity of the resulting amplification. To increase the specificity of the amplification using the degenerate primers, the pools are synthesized as subsets such that the entire group of subsets includes all possible DNA sequences encoding the given amino acid sequence, but each individual subset only includes a portion: for example, one pool may contain either a G or C at a particular position while the other contains either an A or T at the same position. Each of these subpools is designated with a DG number.

Both forward primers (directed from the 5' region toward the 3' region of the gene, complementary to the noncoding strand) and reverse primers (directed from the 3' region toward the 5' region of the gene, complementary to the coding strand) were designed for most of these conserved regions to clone Tma polymerase. The primers were designed with restriction sites at the 5' ends to facilitate cloning. The forward primers contained a BglII restriction site (AGATCT), while the reverse primers contained an EcoRI restriction site (GAATTC). In addition, the primers contained 2 nucleotides at the 5' end to increase the efficiency of cutting at the restriction site.

Degenerate primers were then used in PCR processes in which the target nucleic acid was chromosomal DNA from *Thermotoga maritima*. The products of the PCR processes using a combination of forward and reverse primer pools in conjunction with a series of temperature profiles were compared. When specific products of similar size to the product generated using Taq chromosomal DNA were produced, the PCR fragments were gel purified, reamplified and cloned into the vector BSM13H3:BglII (a derivative of the Stratagene vector pBSM+ in which the HindIII site of pBSM+ was converted to a BglII site). Sequences were identified as potential thermostable DNA polymerase coding sequences if the sequences were found to encode amino acid sequences homologous to other known amino acid sequences in polymerase proteins, particularly those of Taq polymerase and Tth polymerase.

The portions of the Tma DNA polymerase gene were then identified in the chromosomal DNA of *Thermotoga maritima* by Southern blot analysis. The Tma chromosomal DNA was digested with a variety of enzymes and transferred to nitrocellulose filters. Probes labeled with $^{32}P$ or biotin-dUTP were generated for various regions of the gene from the cloned PCR products. The probes were hybridized to the nitrocellulose-bound genomic DNA, allowing identification of the size of the chromosomal DNA fragment hybridizing to the probe. The use of probes covering the 5' and 3' regions of the gene ensures that the DNA fragment(s) contain most if not all of the structural gene for the polymerase. Restriction enzymes are identified that can be used to produce fragments that contain the structural gene in a single DNA fragment or in several DNA fragments to facilitate cloning.

Once identified, the chromosomal DNA fragments encoding the Tma DNA polymerase gene were cloned. Chromosomal DNA was digested with the identified restriction enzyme and size fractionated. Fractions containing the desired size range were concentrated, desalted, and cloned in to the BSM13H3:BglII cloning vector. Clones were identified by hybridization using labeled probes generated from the previous cloned PCR products. The PCR products were then analyzed on polyacrylamide gels.

The DNA sequence and amino acid sequence shown above and the DNA compounds that encode those sequences can be used to design and construct recombinant DNA expression vectors to drive expression of Tma DNA polymerase activity in a wide variety of host cells. A DNA compound encoding all or part of the DNA sequence shown above can also be used as a probe to identify thermostable polymerase-encoding DNA from other organisms, and the amino acid sequence shown above can be used to design peptides for use as immunogens to prepare antibodies that can be used to identify and purify a thermostable polymerase.

Whether produced by recombinant vectors that encode the above amino acid sequence or by native *Thermotoga maritima* cells, however, Tma DNA polymerase will typically be purified prior to use in a recombinant DNA technique. The present invention provides such purification methodology.

For recovering the native protein, the cells are grown using any suitable technique. Briefly, the cells are grown in "MMS"-medium containing (per liter): NaCl (6.93 g); MgSO$_4$.7H$_2$O (1.75 g); MgCl$_2$.6H$_2$O (1.38 g); KCl (0.16 g); NaBr (25 mg); H$_3$BO$_3$ (7.5 mg); SrCl$_2$.6H$_2$O (3.8 mg); KI (0.025 mg); CaCl$_2$ (0.38 g); KH$_2$PO$_4$ (0.5 g); Na$_2$S (0.5 g); (NH$_4$)$_2$Ni(SO$_4$)$_2$ (2 mg); trace minerals (Balch et al., 1979, *Microbiol. Rev.* 43: 260–296) (15 ml); resazurin (1 mg); and starch (5 g) at a pH of 6.5 (adjusted with H$_2$SO$_4$). For growth on solid medium, 0.8% agar (Oxoid) may be added to the medium. Reasonable growth of the cells also occurs in "SME"-medium (Stetter et al., 1983, *Syst. Appl. Microbiol.* 4: 535–551) supplemented with 0.5% yeast extract, or in marine broth (Difco 2216).

After cell growth, the isolation and purification of the enzyme takes place in six stages, each of which is carried out at a temperature below room temperature, preferably about 0° C. to about 4° C., unless stated otherwise. In the first stage or step, the cells, if frozen, are thawed, lysed in an Aminco french pressure cell (8–20,000 psi), suspended in a buffer at about pH 7.5, and sonicated to reduce viscosity.

In the second stage, ammonium sulfate is added to the lysate to prevent the Tma DNA polymerase from binding to DNA or other cell lysate proteins. Also in the second stage, Polymin P (polyethyleneimine, PEI) is added to the lysate to precipitate nucleic acids, and the lysate is centrifuged.

In the third step, ammonium sulfate is added to the supernatant, and the supernatant is loaded onto a phenyl sepharose column equilibrated with a buffer composed of TE (50 mM Tris-Cl, pH 7.5, and 1 mM EDTA) containing 0.3M ammonium sulfate and 0.5 mM DTT (dithiothreitol). The column is then washed first with the same buffer, second with TE-DTT (without ammonium sulfate), third with ethylene glycol-TE-DTT, and finally with 2M urea in TE-DTT containing ethylene glycol. Unless the capacity of the phenylsepharose is exceeded (i.e. by loading more than ~20–30 mg of protein per ml of resin) all of the Tma polymerase activity is retained by the column and elutes with the 2M urea in TE-DTT containing ethylene glycol.

In the fourth stage, the urea eluate is applied to a heparin sepharose column which is equilibrated with 0.08M KCl, 50 mM Tris-Cl (pH 7.5), 0.1 mM EDTA, 0.2% Tween 20 and 0.5 mM DTT. The column is then washed in the same buffer and the enzyme eluted with a linear gradient of 0.08M to 0.5M KCl buffer. The peak activity fractions were found at 0.225M to 0.275M KCl.

In the fifth stage, the fraction collected in the fourth stage is diluted with affigel-blue buffer without KCl and applied to an affigel-blue column equilibrated in 25 mM Tris-Cl (pH 7.5), 0.1 mM EDTA, 0.2% Tween 20, 0.5 mM DTT, and 0.15M KCl. The column is washed with the same buffer and eluted with a linear gradient of 0.15M to 0.7M KCl in the same buffer. The peak activity fractions were found at the 0.3M to 0.55M KCl section of the gradient. These fractions of peak activity are then tested for contaminating deoxyribonucleases (endonucleases and exonucleases) using any suitable procedure. As an example, endonuclease activity may be determined electrophoretically from the change in molecular weight of phage λ DNA or supercoiled plasmid DNA after incubation with an excess of DNA polymerase. Similarly, exonuclease activity may be determined electrophoretically from the change in molecular weight of restriction enzyme digested DNA after incubation with an excess of DNA polymerase. The fractions that have no deoxyribonuclease activity are pooled and diafiltered into phosphocellulose buffer containing 50 mM KCl.

Finally, in a sixth stage, the diafiltered pool from stage five is loaded onto a phosphocellulose column equilibrated to the correct pH and ionic strength of 25 mM Tris-Cl (pH 7.5), 50 mM KCl, 0.1 mM EDTA, 0.2% Tween 20, and 0.5 mM DTT. The column is then washed with the same buffer and eluted with a linear 0.05M to 0.5M KCl gradient. The peak fractions eluted between 0.215M and 0.31M KCl. An undegraded, purified DNA polymerase from these fractions is evidenced by an unchanged migration pattern in an in situ activity gel.

The molecular weight of the DNA polymerase purified from *Thermotoga maritima* may be determined by any technique, for example, by SDS-PAGE analysis using protein molecular weight markers or by calculation from the coding sequence. The molecular weight of the DNA polymerase purified from *Thermotoga maritima* is determined by SDS-PAGE to be about 97 kDa. Based on the predicted amino acid sequence, the molecular weight is estimated at about 102 kDa. The purification protocol of native Tma DNA polymerase is described in more detail in Example 1. Purification of the recombinant Tma polymerase of the invention can be carried out with similar methodology.

Biologically active recombinant Tma polymerases of various molecular weights can be prepared by the methods and vectors of the present invention. Even when the complete coding sequence of the Tma DNA polymerase gene is present in an expression vector in *E. coli*, the cells produce a truncated polymerase, formed by translation starting with the methionine codon at position 140. One can also use recombinant means to produce a truncated polymerase corresponding to the protein produced by initiating translation at the methionine codon at position 284 of the Tma coding sequence. The polymerase lacking amino acids 1 though 139 (about 86 kDa), and the polymerase lacking amino acids 1 through 283 (about 70 kDa) of the wild type Tma polymerase retain polymerase activity but have attenuated 5'→3' exonuclease activity. In addition, the 70 kDa polymerase is significantly more thermostable than native Tma polymerase.

Thus, the entire sequence of the intact Tma DNA polymerase I enzyme is not required for activity. Portions of the Tma DNA polymerase I coding sequence can be used in recombinant DNA techniques to produce a biologically active gene product with DNA polymerase activity. The availability of DNA encoding the Tma DNA polymerase sequence provides the opportunity to modify the coding sequence so as to generate mutein (mutant protein) forms also having DNA polymerase activity. The amino(N)-terminal portion of the Tma polymerase is not necessary for polymerase activity but rather encodes the 5'→3' exonuclease activity of the protein. Using recombinant DNA methodology, one can delete approximately up to one-third of the N-terminal coding sequence of the Tma gene, clone, and express a gene product that is quite active in polymerase assays but, depending on the extent of the deletion, has no 5'→3' exonuclease activity. Because certain N-terminal shortened forms of the polymerase are active, the gene constructs used for expression of these polymerases can include the corresponding shortened forms of the coding sequence.

In addition to the N-terminal deletions, individual amino acid residues in the peptide chain of Tma polymerase may be modified by oxidation, reduction, or other derivation, and the protein may be cleaved to obtain fragments that retain activity. Such alterations that do not destroy activity do not remove the protein from the definition of a protein with Tma polymerase activity and so are specifically included within the scope of the present invention.

Modifications to the primary structure of the Tma DNA polymerase coding sequence by deletion, addition, or alteration so as to change the amino acids incorporated into the Tma DNA polymerase during translation of the mRNA produced from that coding sequence can be made without destroying the high temperature DNA polymerase activity of the protein. Such substitutions or other alterations result in the production of proteins having an amino acid sequence encoded by DNA falling within the contemplated scope of the present invention. Likewise, the cloned genomic sequence, or homologous synthetic sequences, of the Tma DNA polymerase gene can be used to express a fusion polypeptide with Tma DNA polymerase activity or to express a protein with an amino acid sequence identical to that of native Tma DNA polymerase. In addition, such expression can be directed by the Tma DNA polymerase gene control sequences or by a control sequence that functions in whatever host is chosen to express the Tma DNA polymerase.

Thus, the present invention provides a coding sequence for Tma DNA polymerase from which expression vectors applicable to a variety of host systems can be constructed and the coding sequence expressed. Portions of the Tma polymerase-encoding sequence are also useful as probes to retrieve other thermostable polymerase-encoding sequences in a variety of species. Accordingly, oligonucleotide probes that encode at least four to six amino acids can be synthesized and used to retrieve additional DNAs encoding a thermostable polymerase. Because there may not be an exact match between the nucleotide sequence of the thermostable DNA polymerase gene of *Thermotoga maritima* and the corresponding gene of other species, oligomers containing approximately 12–18 nucleotides (encoding the four to six amino sequence) are usually necessary to obtain hybridization under conditions of sufficient stringency to eliminate false positives. Sequences encoding six amino acids supply ample information for such probes. Such oligonucleotide probes can be used as primers in the degenerate priming method of the invention to obtain thermostable polymerase encoding sequences.

The present invention, by providing coding sequences and amino acid sequences for Tma DNA polymerase, therefore enables the isolation of other thermostable polymerase enzymes and the coding sequences for those enzymes. The amino acid sequence of the Tma DNA polymerase I protein is very similar to the amino acid sequences for the thermostable DNA polymerases of Taq and Tth. These similarities facilitated the identification and isolation of the Tma DNA polymerase coding sequence. The areas of similarity in the coding sequences of these three thermostable DNA polymerases can be readily observed by aligning the sequences.

However, regions of dissimilarity between the coding sequences of the three thermostable DNA polymerases can also be used as probes to identify other thermostable polymerase coding sequences that encode thermostable polymerase enzymes. For example, the coding sequence for a thermostable polymerase having some properties of Taq and other divergent properties of Tma may be identified by using probes directed to sequences that encode the regions of dissimilarity between Taq and Tma. Specifically, such regions include a stretch of four or more contiguous amino acids from any one or more of the following regions, identified by amino acid sequence coordinates (numbering is inclusive): 5–10, 73–79, 113–119, 134–145, 191–196, 328–340, 348–352, 382–387, 405–414, 467–470, 495–499, 506–512, 555–559, 579–584, 595–599, 650–655, 732–742, 820–825, 850–856. These regions may be considered as "hallmark motifs" and define additional regions of critical amino acid signature sequences for thermostable DNA polymerase functions (e.g. 5'→3' exonuclease activity, 3'→5' exonuclease activity, and DNA polymerase activity).

One property found in the Tma DNA polymerase, but lacking in native Taq DNA polymerase and native Tth DNA polymerase, is 3'→5' exonuclease activity. This 3'→5' exonuclease activity is generally considered to be desirable, because misincorporated or unmatched bases of the synthesized nucleic acid sequence are eliminated by this activity. Therefore, the fidelity of PCR utilizing a polymerase with 3'→5' exonuclease activity (e.g. Tma DNA polymerase) is increased. The 3'→5' exonuclease activity found in Tma DNA polymerase also decreases the probability of the formation of primer/dimer complexes in PCR. The 3'→5' exonuclease activity in effect prevents any extra dNTPs from attaching to the 3' end of the primer in a non-template dependent fashion by removing any nucleotide that is attached in a non-template dependent fashion. The 3'→5' exonuclease activity can eliminate single-stranded DNAs, such as primers or single-stranded template. In essence, every 3'-nucleotide of a single-stranded primer or template is treated by the enzyme as unmatched and is therefore degraded. To avoid primer degradation in PCR, one can add phosphorothioate to the 3' ends of the primers. Phosphorothioate modified nucleotides are more resistant to removal by 3'→5' exonucleases.

A "motif" or characteristic "signature sequence" of amino acids critical for 3'→5' exonuclease activity in thermostable DNA polymerases can be defined as comprising three short domains. Below, these domains are identified as A, B, and C, with critical amino acid residues shown in one letter abbreviation and non-critical residues identified as "x."

| Domain | Sequence | Representative Tma Coordinates |
| --- | --- | --- |
| A | DxExxxL | 323–329 |
| B | NxxxDxxxL | 385–393 |
| C | YxxxD | 464–468 |

The distance between region A and region B is 55–65 amino acids. The distance between region B and region C is 67–75 amino acids, preferably about 70 amino acids. In Tma DNA polymerase, the amino acids that do not define the critical motif signature sequence amino acids are L and TSS, respectively, in domain A; LKF and YKV, respectively, in domain B; and SCE in domain C. Domain A is therefore DLETSSL; domain B is NLKFDYKVL; and domain C is YSCED in Tma DNA polymerase I. Thus, the present invention provides a thermostable DNA polymerase possessing 3'→5' exonuclease activity that comprises domains A, B, and C, and, more particularly comprises the sequence D-X-E-X$^3$-L-X$^{55-65}$-N-X$^3$-D-X$^3$-L-X$^{65-75}$-Y-X$^3$-D, where one letter amino acid abbreviation is used, and X$^N$ represents the number (N) of non-critical amino acids between the specified amino acids.

A thermostable 3'→5' exonuclease domain is represented by amino acids 291 through 484 of Tma DNA polymerase. Accordingly, "domain shuffling" or construction of "thermostable chimeric DNA polymerases" may be used to provide thermostable DNA polymerases containing novel properties. For example, substitution of the Tma DNA polymerase coding sequence comprising codons about 291 through about 484 for the *Thermus aquaticus* DNA polymerase I codons 289–422 would yield a novel thermostable DNA polymerase containing the 5'→3' exonuclease domain of Taq DNA polymerase (1–289), the 3'→5' exonuclease domain of Tma DNA polymerase (291–484), and the DNA polymerase domain of Taq DNA polymerase (423–832). Alternatively, the 5'→3' exonuclease domain and the 3'→5' exonuclease domain of Tma DNA polymerase (ca. codons 1–484) may be fused to the DNA polymerase (dNTP binding and primer/template binding domains) portions of Taq DNA polymerase (ca. codons 423–832). The donors and recipients need not be limited to Taq and Tma DNA polymerases. Tth DNA polymerase provides analogous domains as Taq DNA polymerase. In addition, the enhanced/preferred reverse transcriptase properties of Tth DNA polymerase can be further enhanced by the addition of a 3'→5' exonuclease domain as illustrated above.

While any of a variety of means may be used to generate chimeric DNA polymerase coding sequences (possessing novel properties), a preferred method employs "overlap" PCR. In this method, the intended junction sequence is designed into the PCR primers (at their 5'-ends). Following the initial amplification of the individual domains, the various products are diluted (ca. 100 to 1000-fold) and combined, denatured, annealed, extended, and then the final forward and reverse primers are added for an otherwise standard PCR.

Thus, the sequence that codes for the 3'→5' exonuclease activity of Tma DNA polymerase can be removed from Tma DNA polymerase or added to other polymerases that lack this activity by recombinant DNA methodology. One can even replace, in a non-thermostable DNA polymerase, the 3'→5' exonuclease activity domain with the thermostable 3'→5' exonuclease domain of Tma polymerase. Likewise, the 3'→5' exonuclease activity domain of a non-thermostable DNA polymerase can be used to replace the 3'→5' exonuclease domain of Tma polymerase (or any other thermostable polymerase) to create a useful polymerase of the invention. Those of skill in the art recognize that the above chimeric polymerases are most easily constructed by recombinant DNA techniques. Similar chimeric polymerases can be constructed by moving the 5'→3' exonuclease domain of one DNA polymerase to another.

Whether one desires to produce an enzyme identical to native Tma DNA polymerase or a derivative or homologue of that enzyme, the production of a recombinant form of Tma polymerase typically involves the construction of an expression vector, the transformation of a host cell with the vector, and culture of the transformed host cell under conditions such that expression will occur.

To construct the expression vector, a DNA is obtained that encodes the mature (used here to include all chimeras or muteins) enzyme or a fusion of the Tma polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of recombinant Tma polymerase. The Tma polymerase is isolated from the medium or from the cells, although recovery and purification of the protein may not be necessary in some instances.

Each of the foregoing steps can be done in a variety of ways. For example, the desired coding sequence may be obtained from genomic fragments and used directly in appropriate hosts. The construction for expression vectors operable in a variety of hosts is made using appropriate replicons and control sequences, as set forth generally below. Construction of suitable vectors containing the desired coding and control sequences employs standard ligation and restriction techniques that are well understood in the art. Isolated plasmids, DNA sequences, or synthesized oligonucleotides are cleaved, modified, and religated in the form desired. Suitable restriction sites can, if not normally available, be added to the ends of the coding sequence so as to facilitate construction of an expression vector, as exemplified below.

Site-specific DNA cleavage is performed by treating with suitable restriction enzyme (or enzymes) under conditions that are generally understood in the art and specified by the manufacturers of commercially available restriction enzymes. See, e.g., New England Biolabs, Product Catalog. In general, about 1 µg of plasmid or other DNA is cleaved by one unit of enzyme in about 20 µl of buffer solution; in the examples below, an excess of restriction enzyme is generally used to ensure complete digestion of the DNA. Incubation times of about one to two hours at about 37° C. are typical, although variations can be tolerated. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., *Methods in Enzymology*, 1980, 65: 499–560.

Restriction-cleaved fragments with single-strand "overhanging" termini can be made blunt-ended (double-strand ends) by treating with the large fragment of *E. coli* DNA polymerase I (Klenow) in the presence of the four deoxynucleoside triphosphates (dNTPs) using incubation times of about 15 to 25 minutes at 20° C. to 25° C. in 50 mM Tris pH 7.6, 50 mM NaCl, 10 mM $MgCl_2$, 10 mM DTT, and 5 to 10 µM dNTPs. The Klenow fragment fills in at 5' protruding ends, but chews back protruding 3' single strands, even though the four dNTPs are present. If desired, selective repair can be performed by supplying only one of the, or selected, dNTPs within the limitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Synthetic oligonucleotides can be prepared using the triester method of Matteucci et al., 1981, *J. Am. Chem. Soc.* 103: 3185–3191, or automated synthesis methods. Kinasing of single strands prior to annealing or for labeling is achieved using an excess, e.g., approximately 10 units, of polynucleotide kinase to 0.5 µM substrate in the presence of 50 mM Tris, pH 7.6, 10 mM $MgCl_2$, 5 mM dithiothreitol (DTT), and 1 to 2 µM ATP. If kinasing is for labeling of probe, the ATP will contain high specific activity $\gamma$-$^{32}$P.

Ligations are performed in 15–30 µl volumes under the following standard conditions and temperatures: 20 mM Tris-Cl, pH 7.5, 10 mM $MgCl_2$, 10 mM DTT, 33 µg/ml BSA, 10 mM–50 mM NaCl, and either 40 µM ATP and 0.01–0.02 (Weiss) units T4 DNA ligase at 0° C. (for ligation of fragments with complementary single-stranded ends) or 1 mM ATP and 0.3–0.6 units T4 DNA ligase at 14° C. (for "blunt end" ligation). Intermolecular ligations of fragments with complementary ends are usually performed at 33–100 µg/ml total DNA concentrations (5 to 100 nM total ends concentration). Intermolecular blunt end ligations (usually employing a 20 to 30 fold molar excess of linkers, optionally) are performed at 1 µM total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove AP and purify the DNA. Alternatively, religation can be prevented by restriction enzyme digestion of unwanted vector fragments before or after ligation with the desired vector.

For portions of vectors or coding sequences that require sequence modifications, a variety of site-specific primer-directed mutagenesis methods are available. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence of a single-stranded vector, such as pBS13+, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic primer at a temperature that permits hybridization of an exact match to the modified sequence but prevents hybridization with the original strand. Transformants that contain DNA that hybridizes with the probe are then cultured and serve as a reservoir of the modified DNA.

In the constructions set forth below, correct ligations for plasmid construction are confirmed by first transforming *E. coli* strain DG101 or another suitable host with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, *Proc. Natl. Acad. Sci. USA* 62: 1159, optionally following chloramphenicol amplification (Clewell, 1972, *J. Bacteriol.* 110: 667). Another method for obtaining plasmid DNA is described as the "Base-Acid" extraction method at page 11 of the Bethesda Research Laboratories publication *Focus*, volume 5, number 2, and very pure plasmid DNA can be obtained by replacing steps 12 through 17 of the protocol with CsCl/ethidium bromide ultracentrifugation of the DNA. The isolated DNA is analyzed by restriction enzyme digestion and/or sequenced by the dideoxy method of Sanger et al., 1977, *Proc. Natl. Acad. Sci. USA* 74: 5463, as further described by Messing et al., 1981, *Nuc. Acids Res.* 9: 309, or by the method of Maxam et al., 1980, *Methods in Enzymology* 65: 499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of Tma polymerase.

The procaryote most frequently used to express recombinant proteins is *E. coli*. For cloning and sequencing, and for expression of constructions under control of most bacterial promoters, *E. coli* K12 strain MM294, obtained from the *E. coli* Genetic Stock Center under GCSC #6135, can be used as the host. For expression vectors with the $P_LN_{RBS}$ control sequence, *E. coli* K12 strain MC1000 lambda lysogen, $N_7N_{53}cI_{857}$ $SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

However, microbial strains other than *E. coli* can also be used, such as bacilli, for example *Bacillus subtilis*, various species of Pseudomonas, and other bacterial strains, for recombinant expression of Tma DNA polymerase. In such procaryotic systems, plasmid vectors that contain replication sites and control sequences derived from the host or a species compatible with the host are typically used.

For example, *E. coli* is typically transformed using derivatives of pBR322, described by Bolivar et al., 1977, *Gene* 2: 95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems (Chang et al., 1977, *Nature* 198: 1056), the tryptophan (trp) promoter system (Goeddel et al., 1980, *Nuc. Acids Res.* 8: 4057), and the lambda-derived $P_L$ promoter (Shimatake et al., 1981, *Nature* 292: 128) and N-gene ribosome binding site ($N_{RBS}$). A portable control system cassette is set forth in U.S. Pat. No. 4,711, 845, issued Dec. 8, 1987. This cassette comprises a $P_L$ promoter operably linked to the $N_{RBS}$ in turn positioned upstream of a third DNA sequence having at least one restriction site that permits cleavage within six bp 3' of the $N_{RBS}$ sequence. Also useful is the phosphatase A (phoA) system described by Chang et al. in European Patent Publication No. 196,864, published Oct. 8, 1986. However, any available promoter system compatible with procaryotes can be used to construct a Tma expression vector of the invention.

The nucleotide sequence of the Tma insert may negatively affect the efficiency of the upstream ribosomal binding site, resulting in low levels of translated polymerase. The translation of the Tma gene can be enhanced by the construction of "translationally coupled" derivatives of the expression vectors. An expression vector can be constructed with a secondary translation initiation signal and short coding sequence just upstream of the Tma gene coding sequence such that the stop codon for the short coding sequence is "coupled" with the ATG start codon for the Tma gene coding sequence. A secondary translation initiation signal that efficiently initiates translation can be inserted upstream of the Tma gene start codon. Translation of the short coding sequence brings the ribosome into close proximity with the Tma gene translation initiation site, thereby enhancing translation of the Tma gene. For example, one expression system can utilize the translation initiation signal and first ten codons of the T7 bacteriophage major capsid protein (gene 10) fused in-frame to the last six codons of TrpE. The TGA (stop) codon for TrpE is "coupled" with the ATG (start) codon for the Tma gene coding sequence, forming the sequence TGATG. A one base frame-shift is required between translation of the short coding sequence and translation of the Tma coding sequence. These derivative expression vectors can be constructed by recombinant DNA methods.

The redundancy of the genetic code can also be related to a low translation efficiency. Typically, when multiple codons coding the same amino acid occur, one of the possible codons is preferentially used in an organism. Frequently, an organism accumulates the tRNA species corresponding to the preferred codons at a higher level than those corresponding to rarely used codons. If the pattern of codon usage differs between *Thermotoga maritima* and the host cell, the tRNA species necessary for translation of the Tma polymerase gene may be in low abundance. In the Tma coding sequence, arginine is most frequently coded for by the "AGA" codon, whereas this codon is used at low frequency in *E. coli* genes, and the corresponding tRNA is present in low concentration in *E. coli* host cells. Consequently, the low concentration in the *E. coli* host cell of "Arg U" tRNA for the "AGA" condon may limit the translation efficiency of the Tma polymerase gene RNA in *E. coli* host cells. The efficiency of translation of the Tma coding sequence within an *E. coli* host cell may be improved by increasing the concentration of this Arg tRNA species by expressing multiple copies of this tRNA gene in the host cell.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101: 307), other plasmid vectors suitable for yeast expression are known (see, for example, Stinchcomb et al., 1979, *Nature* 282: 39; Tschempe et al., 1980, *Gene* 10: 157; and Clarke et al., 1983, *Meth. Enz.* 101: 300). Control sequences for yeast vectors include promoters for the synthesis of glycolytic enzymes (Hess et al., 1968, *J. Adv. Enzyme Reg.* 7: 149; Holland et al., 1978, *Biotechnology* 17: 4900; and Holland et al., 1981, *J. Biol. Chem.* 256: 1385). Additional promoters known in the art include the promoter for 3-phosphoglycerate kinase (Hitzeman et al., 1980, *J. Biol. Chem.* 255: 2073) and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast Tma expression vectors.

The Tma gene can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273: 113), or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1: 561) are available. Expression systems employing insect cells utilizing the control systems provided by baculovirus vectors have also been described (Miller et al., 1986, *Genetic Engineering* (Setlow et al., eds., Plenum Publishing) 8: 277–297). Insect cell-based expression can be accomplished in *Spodoptera frugipeida*. These systems can also be used to produce recombinant Tma polymerase.

Depending on the host cell used, transformation is done using standard techniques appropriate to such cells. The calcium treatment employing calcium chloride, as described by Cohen, 1972, *Proc. Natl. Acad. Sci. USA* 69: 2110 is used for procaryotes or other cells that contain substantial cell wall barriers. Infection with *Agrobacterium tumefaciens* (Shaw et al., 1983, *Gene* 23: 315) is used for certain plant cells. For mammalian cells, the calcium phosphate precipitation method of Graham and van der Eb, 1978, *Virology* 59: 546 is preferred. Transformations into yeast are carried out according to the method of Van Solingen et al., 1977, *J. Bact.* 130: 946 and Hsiao et al., 1979, *Proc. Natl. Acad. Sci. USA* 76: 3829.

Once the Tma DNA polymerase has been expressed in a recombinant host cell, purification of the protein may be desired. Although a variety of purification procedures can be used to purify the recombinant thermostable polymerase of the invention, fewer steps may be necessary to yield an enzyme preparation of equal purity. Because *E. coli* host proteins are heat-sensitive, the recombinant thermostable Tma DNA polymerase can be substantially enriched by heat inactivating the crude lysate. This step is done in the presence of a sufficient amount of salt (typically 0.3M ammonium sulfate) to ensure dissociation of the Tma DNA polymerase from the host DNA and to reduce ionic interactions of Tma DNA polymerase with other cell lysate proteins. In addition, the presence of 0.3M ammonium sulfate promotes hydrophobic interaction with a phenyl sepharose column. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, such as high ionic strength. A descending salt gradient may then be used to elute the sample.

According to the invention, an aqueous mixture (containing either native or recombinant Tma DNA polymerase) is loaded onto a column containing a relatively strong hydrophobic gel such as phenyl sepharose (manufactured by Pharmacia) or Phenyl TSK (manufactured by Toyo Soda). To promote hydrophobic interaction with a phenyl sepharose column, a solvent is used that contains, for example, greater than or equal to 0.3M ammonium sulfate, with 0.3M being preferred, or greater than or equal to 0.5M NaCl. The column and the sample are adjusted to 0.3M ammonium sulfate in 50 mM Tris (pH 7.5) and 1.0 mM EDTA ("TE") buffer that also contains 0.5 mM DTT, and the sample is applied to the column. The column is washed with the 0.3M ammonium sulfate buffer. The enzyme may then be eluted with solvents that attenuate hydrophobic interactions, such as decreasing salt gradients, ethylene or propylene glycol, or urea. For native Tma DNA polymerase, a preferred embodiment involves washing the column with 2M urea and 20% ethylene glycol in TE-DTT.

For long-term stability, Tma DNA polymerase enzyme can be stored in a buffer that contains one or more non-ionic polymeric detergents. Such detergents are generally those that have a molecular weight in the range of approximately 100 to 250,000 daltons, preferably about 4,000 to 200,000 daltons, and stabilize the enzyme at a pH of from about 3.5 to about 9.5, preferably from about 4 to 8.5. Examples of such detergents include those specified on pages 295–298 of McCutcheon's *Emulsifiers & Detergents*, North American edition (1983), published by the McCutcheon Division of MC Publishing Co., 175 Rock Road, Glen Rock, N.J. (USA) and copending Ser. No. 387,003, filed Jul. 28, 1989, each of which is incorporated herein by reference.

Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, a polyoxyethylated (20) sorbitan monolaurate from ICI Americas Inc., Wilmington, Del., and Iconol NP-40, an ethoxylated alkyl phenol (nonyl) from BASF Wyandotte Corp. Parsippany, N.J.

The thermostable enzyme of this invention may be used for any purpose in which such enzyme activity is necessary or desired. In a particularly preferred embodiment, the enzyme catalyzes the nucleic acid amplification reaction known as PCR. This process for amplifying nucleic acid sequences is disclosed and claimed in U.S. Pat. Nos. 4,683,202 and 4,865,188, each of which is incorporated herein by reference. The PCR nucleic acid amplification method involves amplifying at least one specific nucleic acid sequence contained in a nucleic acid or a mixture of nucleic acids and in the most common embodiment, produces double-stranded DNA.

For ease of discussion, the protocol set forth below assumes that the specific sequence to be amplified is contained in a double-stranded nucleic acid. However, the process is equally useful in amplifying single-stranded nucleic acid, such as mRNA, although in the preferred embodiment the ultimate product is still double-stranded DNA. In the amplification of a single-stranded nucleic acid, the first step involves the synthesis of a complementary strand (one of the two amplification primers can be used for this purpose), and the succeeding steps proceed as in the double-stranded amplification process described below.

This amplification process comprises the steps of:

(a) contacting each nucleic acid strand with four different nucleoside triphosphates and two oligonucleotide primers for each specific sequence being amplified, wherein each primer is selected to be substantially complementary to the different strands of the specific sequence, such that the extension product synthesized from one primer, when separated from its complement, can serve as a template for synthesis of the extension product of the other primer, said contacting being at a temperature that allows hybridization of each primer to a complementary nucleic acid strand;

(b) contacting each nucleic acid strand, at the same time as or after step (a), with a DNA polymerase from *Thermotoga maritima* that enables combination of the nucleoside triphosphates to form primer extension products complementary to each strand of the specific nucleic acid sequence;

(c) maintaining the mixture from step (b) at an effective temperature for an effective time to promote the activity of the enzyme and to synthesize, for each different sequence being amplified, an extension product of each primer that is complementary to each nucleic acid strand template, but not so high as to separate each extension product from the complementary strand template;

(d) heating the mixture from step (c) for an effective time and at an effective temperature to separate the primer extension products from the templates on which they were synthesized to produce single-stranded molecules but not so high as to denature irreversibly the enzyme;

(e) cooling the mixture from step (d) for an effective time and to an effective temperature to promote hybridization of a primer to each of the single-stranded molecules produced in step (d); and (f) maintaining the mixture from step (e) at an effective temperature for an effective time to promote the activity of the enzyme and to synthesize, for each different sequence being amplified, an extension product of each primer that is complementary to each nucleic acid template produced in step (d) but not so high as to separate each extension product from the complementary strand template. The effective times and temperatures in steps (e) and (f) may coincide, so that steps (e) and (f) can be carried out simultaneously. Steps (d)–(f) are repeated until the desired level of amplification is obtained.

The amplification method is useful not only for producing large amounts of a specific nucleic acid sequence of known sequence but also for producing nucleic acid sequences that are known to exist but are not completely specified. One need know only a sufficient number of bases at both ends of the sequence in sufficient detail so that two oligonucleotide primers can be prepared that will hybridize to different strands of the desired sequence at relative positions along the sequence such that an extension product synthesized from one primer, when separated from the template (complement), can serve as a template for extension of the other primer into a nucleic acid sequence of defined length. The greater the knowledge about the bases at both ends of the sequence, the greater can be the specificity of the primers for the target nucleic acid sequence and the efficiency of the process.

In any case, an initial copy of the sequence to be amplified must be available, although the sequence need not be pure or a discrete molecule. In general, the amplification process involves a chain reaction for producing, in exponential quantities relative to the number of reaction steps involved, at least one specific nucleic acid sequence given that (a) the ends of the required sequence are known in sufficient detail that oligonucleotides can be synthesized that will hybridize to them and (b) that a small amount of the sequence is available to initiate the chain reaction. The product of the chain reaction will be a discrete nucleic acid duplex with termini corresponding to the 5' ends of the specific primers employed.

Any nucleic acid sequence, in purified or nonpurified form, can be utilized as the starting nucleic acid(s), provided it contains or is suspected to contain the specific nucleic acid sequence one desires to amplify. The nucleic acid to be amplified can be obtained from any source, for example, from plasmids such as pBR322, from cloned DNA or RNA, or from natural DNA or RNA from any source, including bacteria, yeast, viruses, organelles, and higher organisms such as plants and animals. DNA or RNA may be extracted from blood, tissue material such as chorionic villi, or amniotic cells by a variety of techniques. See, e.g., Maniatis et al., supra, pp. 280–281. Thus, the process may employ, for example, DNA or RNA, including messenger RNA, which DNA or RNA may be single-stranded or double-stranded. In addition, a DNA-RNA hybrid that contains one strand of each may be utilized. A mixture of any of these nucleic acids can also be employed as can nucleic acids produced from a previous amplification reaction (using the same or different primers). The specific nucleic acid sequence to be amplified can be only a fraction of a large molecule or can be present initially as a discrete molecule, so that the specific sequence constitutes the entire nucleic acid.

The sequence to be amplified need not be present initially in a pure form; the sequence can be a minor fraction of a complex mixture, such as a portion of the β-globin gene contained in whole human DNA (as exemplified in Saiki et al., 1985, *Science* 230: 1530–1534) or a portion of a nucleic acid sequence due to a particular microorganism, which organism might constitute only a very minor fraction of a particular biological sample. The cells can be directly used in the amplification process after suspension in hypotonic buffer and heat treatment at about 90 C–100 C until cell lysis and dispersion of intracellular components occur (generally 1 to 15 minutes). After the heating step, the amplification reagents may be added directly to the lysed cells. The starting nucleic acid sequence can contain more than one desired specific nucleic acid sequence. The amplification process is useful not only for producing large amounts of one specific nucleic acid sequence but also for amplifying simultaneously more than one different specific nucleic acid sequence located on the same or different nucleic acid molecules.

Primers play a key role in the PCR process. The word "primer" as used in describing the amplification process can refer to more than one primer, particularly in the case where there is some ambiguity in the information regarding the terminal sequence(s) of the fragment to be amplified or where one employs the degenerate primer process of the invention. For instance, in the case where a nucleic acid sequence is inferred from protein sequence information, a collection of primers containing sequences representing all possible codon variations based on degeneracy of the genetic code will be used for each strand. One primer from this collection will be sufficiently homologous with the end of the desired sequence to be amplified to be useful for amplification.

In addition, more than one specific nucleic acid sequence can be amplified from the first nucleic acid or mixture of nucleic acids, so long as the appropriate number of different oligonucleotide primers are utilized. For example, if two different specific nucleic acid sequences are to be produced, four primers are utilized. Two of the primers are specific for one of the specific nucleic acid sequences, and the other two primers are specific for the second specific nucleic acid sequence. In this manner, each of the two different specific sequences can be produced exponentially by the present process.

A sequence within a given sequence can be amplified after a given number of amplification cycles to obtain greater specificity in the reaction by adding, after at least one cycle of amplification, a set of primers that are complementary to internal sequences (i.e., sequences that are not on the ends) of the sequence to be amplified. Such primers can be added at any stage and will provide a shorter amplified fragment. Alternatively, a longer fragment can be prepared by using primers with non-complementary ends but having some overlap with the primers previously utilized in the amplification.

Primers also play a key role when the amplification process is used for in vitro mutagenesis. The product of an amplification reaction where the primers employed are not exactly complementary to the original template will contain the sequence of the primer rather than the template, so introducing an in vitro mutation. In further cycles, this mutation will be amplified with an undiminished efficiency because no further mispaired priming is required. The process of making an altered DNA sequence as described above could be repeated on the altered DNA using different primers to induce further sequence changes. In this way, a series of mutated sequences can gradually be produced wherein each new addition to the series differs from the last in a minor way, but from the original DNA source sequence in an increasingly major way.

Because the primer can contain as part of its sequence a non-complementary sequence, provided that a sufficient amount of the primer contains a sequence that is complementary to the strand to be amplified, many other advantages can be realized. For example, a nucleotide sequence that is not complementary to the template sequence (such as, e.g., a promoter, linker, coding sequence, etc.) may be attached at the 5' end of one or both of the primers and so appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

Oligonucleotide primers can be prepared using any suitable method, such as, for example, the phosphotriester and phosphodiester methods described above, or automated embodiments thereof. In one such automated embodiment, diethylphosphoramidites are used as starting materials and can be synthesized as described by Beaucage et al., 1981, *Tetrahedron Letters* 22: 1859–1862. One method for synthesizing oligonucleotides on a modified solid support is described in U.S. Pat. No. 4,458,066. One can also use a primer that has been isolated from a biological source (such as a restriction endonuclease digest).

No matter what primers are used, however, the reaction mixture must contain a template for PCR to occur, because the specific nucleic acid sequence is produced by using a nucleic acid containing that sequence as a template. The first step involves contacting each nucleic acid strand with four different nucleoside triphosphates and two oligonucleotide primers for each specific nucleic acid sequence being amplified or detected. If the nucleic acids to be amplified or detected are DNA, then the nucleoside triphosphates are usually dATP, dCTP, dGTP, and dTTP, although various nucleotide derivatives can also be used in the process. The concentration of nucleoside triphosphates can vary widely. Typically, the concentration is 50 to 200 µM in each dNTP in the buffer for amplification, and $MgCl_2$ is present in the buffer in an amount of 1 to 3 mM to activate the polymerase and increase the specificity of the reaction. However, dNTP concentrations of 1 to 20 µM may be preferred for some applications, such as DNA sequencing or generating radiolabeled probes at high specific activity.

The nucleic acid strands of the target nucleic acid serve as templates for the synthesis of additional nucleic acid strands, which are extension products of the primers. This synthesis can be performed using any suitable method, but generally occurs in a buffered aqueous solution, preferably at a pH of 7 to 9, most preferably about 8. To facilitate synthesis, a molar excess of the two oligonucleotide primers is added to the buffer containing the template strands. As a practical matter, the amount of primer added will generally be in molar excess over the amount of complementary strand (template) when the sequence to be amplified is contained in a mixture of complicated long-chain nucleic acid strands. A large molar excess is preferred to improve the efficiency of the process. Accordingly, primer:template ratios of at least 1000:1 or higher are generally employed for cloned DNA templates, and primer:template ratios of about $10^8$:1 or higher we generally employed for amplification from complex genomic samples.

The mixture of template, primers, and nucleoside triphosphates is then treated according to whether the nucleic acids being amplified or detected are double- or single-stranded. If the nucleic acids are single-stranded, then no denaturation step need be employed prior to the first extension cycle, and the reaction mixture is held at a temperature that promotes hybridization of the primer to its complementary target (template) sequence. Such temperature is generally from about 35° C. to 65° C. or more, preferably about 37° C. to 60° C. for an effective time, generally from a few seconds to five minutes, preferably from 30 seconds to one minute. A hybridization temperature of 35° C. to 70° C. may be used for Tma DNA polymerase. Primers that are 15 nucleotides or longer in length are used to increase the specificity of primer hybridization. Shorter primers require lower hybridization temperatures.

The complement to the original single-stranded nucleic acids can be synthesized by adding Tma DNA polymerase in the presence of the appropriate buffer, dNTPs, and one or more oligonucleotide primers. If an appropriate single primer is added, the primer extension product will be complementary to the single-stranded nucleic acid and will be hybridized with the nucleic acid strand in a duplex of strands of equal or unequal length (depending on where the primer hybridizes to the template), which may then be separated into single strands as described above to produce two single, separated, complementary strands. A second primer would then be added so that subsequent cycles of primer extension would occur using both the original single-stranded nucleic acid and the extension product of the first primer as templates. Alternatively, two or more appropriate primers (one of which will prime synthesis using the extension product of the other primer as a template) can be added to the single-stranded nucleic acid and the reaction carried out.

If the nucleic acid contains two strands, as in the case of amplification of a double-stranded target or second-cycle amplification of a single-stranded target, the strands of nucleic acid must be separated before the primers are hybridized. This strand separation can be accomplished by any suitable denaturing method, including physical, chemical or enzymatic means. One preferred physical method of separating the strands of the nucleic acid involves heating the nucleic acid until complete (>99%) denaturation occurs. Typical heat denaturation involves temperatures ranging from about 80° C. to 105° C. for times generally ranging from about a few seconds to minutes, depending on the composition and size of the nucleic acid. Preferably, the effective denaturing temperature is 90° C.–100° C. for a few seconds to 1 minute. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Berling, 1978, *CSH-Quantitative Biology* 43: 63, and techniques for using RecA are reviewed in Radding, 1982, *Ann. Rev. Genetics* 16: 405–437. The denaturation produces two separated complementary strands of equal or unequal length.

If the double-stranded nucleic acid is denatured by heat, the reaction mixture is allowed to cool to a temperature that promotes hybridization of each primer to the complementary target (template) sequence. This temperature is usually from about 35° C. to 65° C. or more, depending on reagents, preferably 37° C. to 60° C. The hybridization temperature is maintained for an effective time, generally a few seconds to minutes, and preferably 10 seconds to 1 minute. In practical terms, the temperature is simply lowered from about 95° C. to as low as 37° C., and hybridization occurs at a temperature within this range.

Whether the nucleic acid is single- or double-stranded, the DNA polymerase from *Thermotoga maritima* can be added prior to or during the denaturation step or when the temperature is being reduced to or is in the range for promoting hybridization. Although the thermostability of Tma polymerase allows one to add Tma polymerase to the reaction mixture at any time, one can substantially inhibit nonspecific amplification by adding the polymerase to the reaction mixture at a point in time when the mixture will not be cooled below the stringent hybridization temperature. After hybridization, the reaction mixture is then heated to or maintained at a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer that is complementary to each nucleic acid template, but must not be so high as to denature each extension product from its complementary template (i.e., the temperature is generally less than about 80° C. to 90° C.).

Depending on the nucleic acid(s) employed, the typical temperature effective for this synthesis reaction generally ranges from about 40° C. to 80° C., preferably 50° C. to 75° C. The temperature more preferably ranges from about 65° C. to 75° C. for *Thermotoga maritima* DNA polymerase. The period of time required for this synthesis may range from about 10 seconds to several minutes or more, depending mainly on the temperature, the length of the nucleic acid, the enzyme, and the complexity of the nucleic acid mixture. The extension time is usually about 30 seconds to a few minutes. If the nucleic acid is longer, a longer time period is generally required for complementary strand synthesis.

The newly synthesized strand and the complement nucleic acid strand form a double-stranded molecule that is used in the succeeding steps of the amplification process. In the next step, the strands of the double-stranded molecule are separated by heat denaturation at a temperature and for a time effective to denature the molecule, but not at a temperature and for a period so long that the thermostable enzyme is completely and irreversibly denatured or inactivated. After this denaturation of template, the temperature is decreased to a level that promotes hybridization of the primer to the complementary single-stranded molecule (template) produced from the previous step, as described above.

After this hybridization step, or concurrently with the hybridization step, the temperature is adjusted to a temperature that is effective to promote the activity of the thermostable enzyme to enable synthesis of a primer extension product using as a template both the newly synthesized and the original strands. The temperature again must not be so high as to separate (denature) the extension product from its template, as described above. Hybridization may occur during this step, so that the previous step of cooling after denaturation is not required. In such a case, using simultaneous steps, the preferred temperature range is 50° C. to 70° C.

The heating and cooling steps involved in one cycle of strand separation, hybridization, and extension product synthesis can be repeated as many times as needed to produce the desired quantity of the specific nucleic acid sequence. The only limitation is the amount of the primers, thermostable enzyme, and nucleoside triphosphates present. Usually, from 15 to 30 cycles are completed. For diagnostic detection of amplified DNA, the number of cycles will depend on the nature of the sample and the initial target concentration in the sample. For example, fewer cycles will be required if the sample being amplified is pure. If the sample is a complex mixture of nucleic acids, more cycles will be required to amplify the signal sufficiently for detection. For general amplification and detection, the process is repeated about 15 times. When amplification is used to generate sequences to be detected with labeled sequence-specific probes and when human genomic DNA is the target of amplification, the process is repeated 15 to 30 times to amplify the sequence sufficiently so that a clearly detectable signal is produced, i.e., so that background noise does not interfere with detection.

No additional nucleosides, primers, or thermostable enzyme need be added after the initial addition, provided that no key reagent has been exhausted and that the enzyme has not become denatured or irreversibly inactivated, in which case additional polymerase or other reagent would have to be added for the reaction to continue. Addition of such materials at each step, however, will not adversely affect the reaction. After the appropriate number of cycles has been completed to produce the desired amount of the specific nucleic acid sequence, the reaction can be halted in the usual manner, e.g., by inactivating the enzyme by adding EDTA, phenol, SDS, or $CHCl_3$ or by separating the components of the reaction.

The amplification process can be conducted continuously. In one embodiment of an automated process, the reaction mixture can be temperature cycled such that the temperature is programmed to be controlled at a certain level for a certain time. One such instrument for this purpose is the automated machine for handling the amplification reaction developed and marketed by Perkin-Elmer Cetus Instruments. Detailed instructions for carrying out PCR with the instrument are available upon purchase of the instrument.

Tma DNA polymerase is very useful in the diverse processes in which amplification of a nucleic acid sequence by the polymerase chain reaction is useful. The amplification method may be utilized to clone a particular nucleic acid sequence for insertion into a suitable expression vector, as described in U.S. Pat. No. 4,800,159. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers. Other processes suitable for Tma polymerase include those described in U.S. Pat. Nos. 4,683,195 and 4,683,202 and European Patent Publication Nos. 229,701;

237,362; and 258,017; these patents and publications are incorporated herein by reference. In addition, the present enzyme is useful in asymmetric PCR (see Gyllensten and Erlich, 1988, *Proc. Natl. Acad. Sci. USA* 85: 7652–7656, incorporated herein by reference); inverse PCR (Ochman et al., 1988, *Genetics* 120: 621, incorporated herein by reference); and for DNA sequencing (see Innis et al., 1988, *Proc. Natl. Acad. Sci. USA* 85: 9436–9440, and McConlogue et al., 1988, *Nuc. Acids Res.* 16(20): 9869). Tma polymerase is also believed to have reverse transcriptase activity; see PCT Patent Publication No. 91/09944, published Jul. 11, 1991, incorporated herein by reference.

The reverse transcriptase activity of Tma DNA polymerase permits this enzyme to be used in methods for transcribing and amplifying RNA. The improvement of such methods resides in the use of a single enzyme, whereas previous methods have required more than one enzyme.

The improved methods comprise the steps of: (a) combining an RNA template with a suitable primer under conditions whereby the primer will anneal to the corresponding RNA template; and (b) reverse transcribing the RNA template by incubating the annealed primer-RNA template mixture with Tma DNA polymerase under conditions sufficient for the DNA polymerase to catalyze the polymerization of deoxyribonucleoside triphosphates to form a DNA sequence complementary to the sequence of the RNA template.

In another aspect of the above method, the primer that anneals to the RNA template may also be suitable for amplification by PCR. In PCR, a second primer that is complementary to the reverse transcribed cDNA strand provides a site for initiation of synthesis of an extension product. As already discussed above, the Tma DNA polymerase is able to catalyze this extension reaction on a cDNA template.

In the amplification of an RNA molecule by Tma DNA polymerase, the first extension reaction is reverse transcription, in which a DNA strand is produced in the form of an RNA/cDNA hybrid molecule. The second extension reaction, using the DNA strand as a template, produces a double-stranded DNA molecule. Thus, synthesis of a complementary DNA strand from an RNA template with Tma DNA polymerase provides the starting material for amplification by PCR.

When Tma DNA polymerase is used for nucleic acid transcription from an RNA template, the use of buffers that contain $Mn^{2+}$ provide improved stimulation of Tma reverse transcriptase activity compared to previously used, $Mg^{2+}$ containing reverse transcription buffers. Consequently, increased cDNA yields also result from these methods.

As stated above, the product of RNA transcription by Tma DNA polymerase is an RNA/cDNA hybrid molecule. The RNA is then removed by heat denaturation or any number of other known methods including alkali, heat, or enzyme treatment. The remaining cDNA strand then serves as a template for polymerization of a self-complementary strand, thereby providing a double-stranded cDNA molecule suitable for amplification or other manipulation. The second strand synthesis requires a sequence specific primer and Tma DNA polymerase.

Following the synthesis of the second cDNA strand, the resultant double-stranded cDNA molecule can serve a number of purposes, including DNA sequencing, amplification by PCR, or detection of a specific nucleic acid sequence. Specific primers useful for amplification of a segment of the cDNA can be added subsequent to the reverse transcription. Also, one can use a first set of primers to synthesize a specific cDNA molecule and a second nested set of primers to amplify a desired cDNA segment. All of these reactions are catalyzed by Tma DNA polymerase.

Tma DNA polymerase can also be used to simplify and improve methods for detection of RNA target molecules in a sample. In these methods, Tma DNA polymerase catalyzes: (a) reverse transcription; (b) second strand cDNA synthesis; and, if desired (c) amplification by PCR. In addition to the improvement of only requiring a single enzyme, the use of Tma DNA polymerase in the described methods eliminates the previous requirement of two sets of incubation conditions that were necessary due to the use of different enzymes for each procedural step. The use of Tma DNA polymerase provides RNA transcription and amplification of the resulting complementary DNA with enhanced specificity and with fewer steps than previous RNA cloning and diagnostic methods. These methods are adaptable for use in kits for laboratory or clinical analysis.

The RNA that is transcribed and amplified in the above methods can be derived from a number of sources. The RNA template can be contained within a nucleic acid preparation from any organism, such as a viral or bacterial nucleic acid preparation. The preparation can contain cell debris and other components, purified total RNA, or purified mRNA. The RNA template can also be a population of heterogeneous RNA molecules in a sample. Furthermore, the target RNA can be contained in a biological sample, and the sample can be a heterogeneous sample in which RNA is but a small portion. Examples of such biological samples include blood samples and biopsied tissue samples.

Although the primers used in the reverse transcription step of the above methods are generally completely complementary to the RNA template, the primers need not be completely complementary. As in PCR, not every nucleotide of the primer must anneal to the template for reverse transcription to occur. For example, a non-complementary nucleotide sequence can be present at the 5' end of the primer with the remainder of the primer sequence being complementary to the RNA. Alternatively, non-complementary bases can be interspersed into the primer, provided that the primer sequence has sufficient complementarity with the RNA template for hybridization to occur and allow synthesis of a complementary DNA strand.

The following examples are offered by way of illustration only and are by no means intended to limit the scope of the claimed invention. In these examples, all percentages are by weight if for solids and by volume if for liquids, unless otherwise noted, and all temperatures are given in degrees Celsius.

EXAMPLE 1

Purification of *Thermotoga maritima* DNA Polymerase

This example describes the isolation of Tma DNA polymerase from *Thermotoga maritima*. The DNA polymerase was assayed at various points during purification according to the method described for Taq polymerase with one modification (1 mM $MgCl_2$) in Lawyer et al., 1989, *J. Biol. Chem.* 264(11): 6427–6437, incorporated herein by reference.

Typically, this assay is performed in a total volume of 50 µl of a reaction mixture composed of 25 mM TAPS-HCl, pH 9.5 (20° C.); 50 mM KCl; 1 mM $MgCl_2$; 1 mM β-mercaptoethanol; 200 µM in each of dATP, dGTP, and TTP; 100 µM α-$^{32}$P-dCTP (0.03 to 0.07 µCi/nMol); 12.5 µg of activated salmon sperm DNA; and polymerase. The reaction is initiated by addition of polymerase in diluent (diluent is composed of 10 mM Tris-HCl, pH 8.0, 50 mM KCl, 0.1 mM EDTA, 1 mg/ml autoclaved gelatin, 0.5% NP40, 0.5% Tween 20, and 1 mM 13-mercaptoethanol), and the reaction is carried out at 75° C. For the calculations shown below, one assumes that the volume of the polymerase (and diluent) added is 5 µl, and the total reaction volume is 50 µl. After a 10 minute incubation, the reaction is stopped by adding 10 µl of 60 mM EDTA. The reaction mixture is centrifuged, and 50 µl of reaction mixture is transferred to 1.0 ml of 50 µg/ml carrier DNA in 2 mM EDTA (at 0° C). An equal volume (1 ml) of 20% TCA, 2% sodium pyrophosphate is added and mixed. The mixture is incubated at 0° C. for 15 to 20 minutes and then filtered through Whatman GF/C filters and extensively washed (6×5 ml) with a cold mixture containing 5% TCA and 1% pyrophosphate, followed by a cold 95% ethanol wash. The filters are then dried and the radioactivity counted. Background (minus enzyme) is usually 0.001% to 0.01% of input cpm. About 50 to 250 pmoles $^{32}$P-dCTP standard is spotted for unit calculation. One unit is equal to 10 nmoles dNTP incorporated in 30 minutes at 75° C. Units are calculated as follows.

$$\frac{\text{sample cpm} - \text{enzyme } dil. \text{ cpm}}{\text{specific activity of } dCTP \text{ (cpm/pmole)}} = \text{pmole } dCTP \text{ incorporated}$$

$$\frac{\text{pmole incorporated} \times 3 \times \text{dilution factor} \times 4}{4.167 \times 10} = \text{units/ml}$$

The 4.167 factor results from counting only 5/6 (50 µl) of the reaction volume after the stop solution is added (60 µl).

All operations were carried out at 0° C. to 4° C. unless otherwise stated. All glassware was baked prior to use, and solutions used in the purification were autoclaved, if possible, prior to use.

About 50 g of frozen *Thermotoga maritima* strain MSB8 cells (provided by Prof. Dr. K. O. Stetter, Regensburg, Germany) were thawed in 25 ml of 3×TE-DTT buffer (150 mM Tris-Cl, pH 7.5, 3 mM EDTA, and 3 mM dithiothreitol) containing 2.4 mM PMSF (from 144 mM stock in DMF) and homogenized at low speed with a magnetic stirrer. The thawed cells were lysed in an Aminco french pressure cell (8–20,000 psi). The lysate was diluted with additional 1×TE-DTT buffer containing fresh 2.4 mM PMSF to final 5.5×cell wet weight and sonicated to reduce viscosity (40 to 100% output, 9 min., 50% duty cycle).

The resulting fraction, fraction I (275 ml) contained 5.31 g of protein and 15.5×10$^4$ units of activity. Ammonium sulfate was added to 0.2M (7.25 g) and the lysate stirred for 15 minutes on ice. Ammonium sulfate prevents the Tma DNA polymerase from binding to DNA in the crude lysate and reduces ionic interactions of the DNA polymerase with other cell lysate proteins.

Empirical testing showed that 0.2% Polymin P (polyethyleneimine, PEI) precipitates ≧92% of the total nucleic acid. Polymin P (pH 7.5) was added slowly to 0.2% (5.49 ml of 10% PEI) and the slurry stirred 30 minutes on ice, then centrifuged at 30,000×g at 4° C. for 30 minutes. The supernatant was designated fraction II (246 ml) and contained 3.05 g of protein and 12.5×10$^4$ units of activity.

Fraction II was adjusted to 0.3M ammonium sulfate by addition of 3.24 g solid ammonium sulfate to ensure complete binding of the DNA polymerase to phenyl sepharose. Fraction II was then loaded onto a 2.2×6.6 cm (25 ml) phenyl sepharose CL-4B (lot OM 08012, purchased from Pharmacia—LKB) column (equilibrated in TE containing 0.3M ammonium sulfate and 0.5 mM DTT) at 38 ml/hr (10 ml/cm$^2$/hr). All resins were equilibrated and recycled according to the manufacturer's recommendations.

The column was washed with 150 ml of the same buffer ($A_{280}$ to baseline), then with 90 ml TE containing 0.5 mM DTT (no ammonium sulfate), followed by a wash with 95 ml of 20% ethylene glycol in TE containing 0.5 mM DTT and finally, eluted with 2M urea in TE containing 20% ethylene glycol and 0.5 mM DTT. When the column fractions were assayed, a large proportion of the activity was found in the flow-through and wash fractions, indicating that the capacity of the column had been exceeded. Approximately 70% of the DNA polymerase which had bound to this first phenyl sepharose column eluted at low salt (with the TE-DTT wash), and the balance of the bound material eluted with 2M urea in 20% ethylene glycol in TE-DTT wash.

The flow-through activity from the first phenyl sepharose column was designated PSII load (226 ml) and contained 1.76 g protein. Fraction PSII load was applied to a second phenyl sepharose column (of the same lot and dimensions), and the run was repeated the same way. Again, the capacity of the column was exceeded, and activity was found to elute with both the low salt and 2M urea washes. Only 10% of the bound DNA polymerase eluted with the TE-DTT wash; the major portion (~90%) eluted with the 2M urea in 20% ethylene glycol in TE-DTT wash.

The flow-through activity from the second phenyl sepharose column was combined with the TE-DTT eluates from the first and second phenyl sepharose columns and adjusted to 0.3M ammonium sulfate. This fraction (PSIII load, 259.4 ml) contained 831 mg protein and was reapplied to a third phenyl sepharose column of 50 ml bed volume at 10 ml/cm$^2$/hr. This time, all of the applied activity was retained by the column and only eluted with the 2M urea in 20% ethylene glycol in TE-DTT wash.

All three urea eluates were separately concentrated ~3 to 4 fold on Amicon YM30 membranes and dialyzed into heparin sepharose loading buffer shortly after elution to avoid prolonged exposure to urea (to avoid carbamylation). The dialyzed and concentrated urea eluates were assayed for protein concentration and were found to vary greatly in their specific activity. Because the urea eluate from the second phenyl sepharose column contained the majority of the activity at significantly higher specific activity (~8×10$^4$ units of activity at ~1000 units/mg protein) than the other two eluates, it was processed separately from them.

The dialyzed and concentrated phenyl sepharose II urea eluate was applied to a 5 ml bed volume heparin sepharose CL 6B (purchased from Pharmacia—LKB) column that had been equilibrated with 0.08M KCl, 50 mM Tris-Cl, pH 7.5, 0.1 mM EDTA, 0.2% Tween 20, and 0.5 mM DTT. This column and all subsequent columns were run at 1 bed volume per hr. All of the applied DNA polymerase activity was retained by the column. The column was washed with 17 ml of the same buffer ($A_{280}$ to baseline) and eluted with 60 ml of a linear 80 to 500 mM KCl gradient in the same buffer.

Fractions (0.53 ml) eluting between 0.21 and 0.315M KCl were analyzed by SDS-PAGE. The peak fractions eluting between 0.225 and 0.275M KCl were pooled separately. The flanking fractions were kept to be combined later with other fractions. The pool of peak fractions (affigel I load) was diluted with affigel-blue buffer without KCl to reduce its ionic strength to 0.15M KCl.

The affigel I load fraction contained 3.4 mg of protein and was applied to a 4.3 ml affigel-blue (purchased from BioRad) column, which had been equilibrated in 25 mM Tris-Cl, pH 7.5, 0.1 mM EDTA, 0.2% Tween 20, 0.5 mM DTT, and 0.15M KCl. All of the applied Tma DNA polymerase was retained. The column was washed with 15 ml of the same buffer and eluted with a 66 ml linear 0.15 to 0.7M KCl gradient in the same buffer.

Fractions (0.58 ml) eluting between 0.34 and 0.55M KCl were analyzed by SDS-PAGE and appeared to be >90% pure. The polymerase peak fractions were no longer contaminated with site-specific endonuclease (indicated by absence of lower-molecular-weight specific DNA fragments after one or twenty-two hours incubation at 65° C. with 2 units of Tma polymerase using 600 ng of plasmid pLSG 1 (ccc-DNA)). The polymerase peak fractions eluting between 0.3 and 0.55M were pooled and concentrated ~20-fold on an Amicon YM 30 membrane. This fraction was then diafiltered into 2.5×storage buffer (50 mM Tris-Cl, pH 7.5, 250 mM KCl, 0.25 mM EDTA, 2.5 mM DTT, and 0.5% Tween 20 [Pierce, Surfact-Amps]) and stored at 4° C.

The urea eluates from the first and third phenyl sepharose columns were combined with the flanking fractions from the first heparin sepharose column. This pool (HSII load) contained ~200 mg protein and was diluted with heparin sepharose buffer without KCl to adjust its ionic strength to 80 mM KCl. HSII load was applied to a 16 ml bed volume heparin sepharose column (equilibrated in 80 mM KCl, 50 mM Tris-Cl, pH 7.5, 0.1 mM EDTA, 0.2% Tween 20, and 0.5 mM DTT). No detectable polymerase activity appeared in the flow-through fractions.

The column was washed with 80 ml of the same buffer and eluted with a 200 ml linear 80 to 750 mM KCl gradient in the same buffer. Fractions (2 ml) eluting between 0.225 and 0.335M KCl were combined, concentrated ~5-fold on an Amicon YM 30 membrane, and dialyzed into hydroxyapatite-buffer. This fraction (HA load) contained 9.3 mg protein and was loaded onto a 4 ml bed volume hydroxyapatite (high resolution HPT, purchased from Calbiochem) column that had been equilibrated in 10 mM potassium phosphate buffer, pH 7.5, 0.5 mM DTT, 0.1 mM EDTA, and 0.2% Tween 20. All of the applied DNA polymerase activity was retained by the column.

The column was washed with 12 ml of the same buffer and eluted with a 60 ml linear 10 to 500 mM potassium phosphate (pH 7.5) gradient. Fractions (0.8 ml) eluting between 0.105 and 0.230M potassium phosphate were analyzed by SDS-PAGE. Compared to the affigel column I load fraction (which by SDS-PAGE appeared to be ~10 to 20% pure), these fractions were ~5-fold less pure. The DNA polymerase peak fractions eluting between 0.105 and 0.255M potassium phosphate were combined, concentrated ~3-fold on an Amicon YM 30 membrane, and diafiltered into affigel-blue buffer.

The affigel II load fraction was applied to a 3 ml bed volume affigel-blue column that had been equilibrated in affigel-blue buffer. No detectable DNA polymerase activity appeared in the flow-through fractions. The column was washed with 9 ml of the same buffer and eluted with a 50 ml linear 0.2 to 0.7M KCl gradient in the same buffer. Fractions (0.58 ml) eluting between 0.33 and 0.505M KCl were analyzed by SDS-PAGE. Because the earlier eluting fractions looked slightly cleaner by their silver staining pattern, two pools were made. Fractions eluting between 0.31 and 0.4M KCl were combined into pool I; fractions eluting between 0.4 and 0.515M KCl were combined into pool II. The two pools were each separately concentrated ~7-fold on an Amicon YM 30 membrane.

All three affigel-blue pools still contained high levels of contaminating, non-specific nucleases. Upon incubation at 70° C. with 1.5 units of DNA polymerase, both a single-strand M13 DNA template and a multifragment restriction digest of a plasmid were degraded within a few hours. In situ-activity gels were run and showed that the DNA polymerase fractions had not suffered proteolytic degradation.

The two pools from the second affigel-blue column were combined and dialyzed into a phosphocellulose column buffer. The dialyzed fraction (Pll I load) was loaded onto a 3 ml phosphocellulose column, which had been washed overnight with 25 mM Tris-Cl, pH 7.5, 50 mM KCl, 0.1 mM EDTA, 0.2% Tween 20, and 0.5 mM DTT. This wash later proved to have been insufficient to equilibrate the pH of the phosphocellulose resin. Unfortunately, this was discovered after the sample had been loaded onto the column. All of the applied activity bound to the column.

The column was washed with 9 ml of loading buffer and eluted with a 45 ml linear 50 to 700 mM KCl gradient. DNA polymerase peak fractions (0.58 ml) eluting between 0.46 and 0.575M KCl were analyzed by SDS-PAGE.

Separation of contaminating proteins was observed throughout the peak: a ~45 kDa contaminating band elutes at 0.53M KCl; an ~85 kDa contaminating band has an elution peak at 0.54M KCl. Therefore, this column was repeated (loading at somewhat higher ionic strength considering the elution profile of the polymerase). The peak fractions, eluting between 0.475 and 0.56M KCl from the first phosphocellulose column were combined with the pool from the first affigel column. The combined fraction (Pll II load) now contained all of the purified polymerase (~7.5× $10^4$ units).

Fraction Pll II load was diluted with phosphocellulose buffer to adjust its ionic strength to 0.2M KCl. Pll II load was loaded onto a 9 ml bed volume phosphocellulose column, which, this time, had been equilibrated to the correct pH and ionic strength of 25 mM Tris-Cl, pH 7.5, 200 mM KCl, 0.1 mM EDTA, 0.2% Tween 20, and 0.5 mM DTT. The column was washed with 27 ml of the same buffer and was intended to be eluted with a 140 ml linear 0.2 to 0.8M KCl gradient. However, instead of an upper limit buffer of 0.8M KCl, the buffer had a concentration of 52 mM KCl which resulted in a gradient decreasing in salt. The column was then reequilibrated with 32 ml of 0.2M KCl-phosphocellulose buffer, and the 140 ml linear 0.2 to 0.8M KCl gradient was reapplied.

The routine assays of flow-through, wash, and gradient fractions showed that, at this higher pH (pH 7.5), the DNA polymerase does not bind to the phosphocellulose resin at 0.2M KCl. The DNA polymerase activity containing fractions from the flow-through, wash, and decreasing salt-gradient-fractions were combined. The resulting pool was concentrated on an Amicon YM30 membrane. However, a mishap with the concentrator led to further losses of DNA polymerase activity. The recovered activity was dialyzed into phosphocellulose buffer with 50 mM KCl and designated Pll III load.

This fraction was loaded onto a 5 ml bed volume phosphocellulose column that had been equilibrated with phosphocellulose buffer with 50 mM KCl. All of the applied activity was retained by the column. The column was washed with 15 ml of the same buffer and eluted with a 45 ml linear 50 to 500 mM KCl gradient in the same buffer. Fractions (0.87 ml) eluting between 0.16 and 0.33M KCl were analyzed by SDS-PAGE and in situ activity gels.

Based on the silver staining pattern, two pools were made. The peak fractions, eluting between 0.215 and 0.31M KCl, were kept separate from the leading and trailing fractions, which were combined into a side-fractions pool. Both pools were concentrated on centricon 30 membranes and diafiltered into 2.5×storage buffer (50 mM Tris-HCl, pH 7.5, 250 mM KCl, 0.25 mM EDTA, 2.5 mM DTT, and 0.5% Tween 20 [Pierce, Surfact-Amps]) and subsequently mixed with 1.5 volumes of 80% glycerol.

About $3.1 \times 10^4$ units were recovered in the peak fraction; the side pool yields an additional $1 \times 10^3$ units of activity. The purified DNA polymerase was undegraded as evidenced by an unchanged migration pattern in an in situ activity gel. The molecular weight as determined by gel electrophoresis of the purified DNA polymerase is approximately 97 kDa. Tma DNA polymerase is recognized by epitope-specific antibodies that correspond to Taq DNA polymerase amino acid residues number 569 through 587 (DGTP1) and 718 through 732 (DGTP3).

EXAMPLE 2

Isolation of DNA Encoding Tma DNA Polymerase I Activity

Synthetic oligodeoxyribonucleotides DG164 through DG167 are four different 16-fold degenerate (each) 22 mer pools designed as "forward" primers to one of the motifs in the template binding domains (3'-most 14 nucleotides) of thermostable DNA polymerases. This motif is the amino acid sequence Gly-Tyr-Val-Glu-Thr and corresponds identically to the *T. aquaticus* (Taq) DNA polymerase amino acids 718 through 722 and to the *T. thermophilus* (Tth) DNA polymerase amino acids 720 through 724. This motif is found in a DNA polymerase gene in all Thermus species. The combined primer pool is 64-fold degenerate, and the primers encode a BglII recognition sequence at their 5'-ends.

Forward primers DG164 through DG167 are shown below:

| DG164 | SEQ ID NO: 2 | 5'CGAGATCTGGNTAYGTWGAAAC |
|---|---|---|
| DG165 | SEQ ID NO: 3 | 5'CGAGATCTGGNTAYGTWGAGAC |
| DG166 | SEQ ID NO: 4 | 5'CGAGATCTGGNTAYGTSGAAAC |
| DG167 | SEQ ID NO: 5 | 5'CGAGATCTGGNTAYGTSGAGAC |

In these forward primers: A is Adenine; C is Cytidine; G is Guanidine; T is Thymine; Y is C+T (pYrimidine); S is G+C (Strong interaction; 3 H-bonds); W is A+T (Weak interaction; 2 H-bonds); and N is A+C+G+T (aNy).

Synthetic oligodeoxyribonucleotides DG160 through DG163 are four different 8-fold degenerate (each) 20 mer pools designed as "reverse" primers to one of the motifs in the template binding domains (3'-most 14 nucleotides) of thermostable DNA polymerases. These primers are designed to complement the (+)-strand DNA sequence that encodes the motif Gln-Val-His-Asp-Glu and that corresponds identically to the Taq DNA polymerase amino acids 782 through 786 and to the Tth. DNA polymerase amino acids 784 through 788. This motif is found in a DNA polymerase gene in all Thermus species. The combined primer pool is 32-fold degenerate, and the primers encode an EcoRI recognition sequence at their 5'-ends.

Reverse primers DG160 through 163 are shown below:

| DG160 | SEQ ID NO: 6 | 5'CGGAATTCRTCRTGWACCTG |
|---|---|---|
| DG161 | SEQ ID NO: 7 | 5'CGGAATTCRTCRTGWACTTG |
| DG162 | SEQ ID NO: 8 | 5'CGGAATTCRTCRTGSACCTG |
| DG163 | SEQ ID NO: 9 | 5'CGGAATTCRTCRTGSACTTG |

In these reverse primers A, C, G, T, S, and W are as defined above, and R is G+A (puRine).

To amplify an ~230 bp fragment of the Tma DNA polymerase gene, a PCR amplification tube was prepared without MgCl$_2$ that contained in 80 µl: (1) 5 ng denatured Tma genomic DNA; (2) 50 pmoles (total) of the combined forward primer set DG164–DG167; (3) 50 pmoles (total) of the combined reverse primer set DG 160–DG163; (4) 2 units Taq DNA polymerase; (5) 50 µM each (final) dNTP; (6) 0.05% Laureth-12; and (7) standard PCR buffer except no magnesium chloride.

The sample was flash-frozen at −70° C. and then stored at −20° C. The frozen sample was carefully layered with 20 µl of 10 mM MgCl$_2$ (final concentration 2 mM), immediately overlayed with 50 µl of mineral oil, and cycled in a Perkin Elmer Cetus Thermal Cycler according to the following file: (1) step to 98° C.—hold 50 seconds; (2) step to 50° C.—hold 10 seconds; (3) ramp to 75° C. over 4 minutes; and (4) step to 98° C. The file was repeated for a total of 30 cycles. One-fifth (20 µl) of the amplification product was purified on a 3% Nusieve/1% Seakem agarose composite gel, and the approximately 230 bp fragment was eluted, concentrated, and digested with BglII and EcoRI.

Synthetic oligodeoxyribonucleotides DG154 and DG155 are two different 32-fold degenerate (each) 19 mer pools designed as "forward" primers to one of the motifs in the primer:template binding domains (3'-most 11 nucleotides) of thermostable DNA polymerases. This motif is the tetrapeptide sequence Thr-Ala-Thr-Gly and corresponds identically to the Taq DNA polymerase amino acids 569 through 572 and to Tth DNA polymerase amino acids 571 through 574. This motif is found in a DNA polymerase gene in all Thermus species. The combined primer pool is 64-fold degenerate and the primers encode a BglII recognition sequence at their 5'-ends.

Forward primers DG154 and DG155 are presented below:

| DG154 | SEQ ID NO: 10 | CGAGATCTACNGCNACWGG |
|---|---|---|
| DG155 | SEQ ID NO: 11 | CGAGATCTACNGCNACSGG |

In these forward primers, A, C, G, T, S, W, and N are as defined above.

To amplify an approximately ~667 bp fragment of the Tma DNA polymerase gene, a PCR amplification tube was prepared without MgCl$_2$ that contained, in 80 µl: (1) 5 ng denatured Tma genomic DNA; (2) 50 pmoles (total) of the combined forward primer set DG154–DG155; (3) 50 pmoles (total) of the combined reverse primer set DG160–DG163; (4) 2 Units of Taq DNA polymerase; (5) 50 µM each (final) dNTP; (6) 0.05% Laureth 12; and (7) standard PCR buffer except no magnesium chloride.

The sample was flash-frozen at −70° C. and then stored at −20° C. The frozen sample was carefully layered with 20 µl of 10 mM MgCl$_2$ (final concentration 2 mM), immediately overlayed with 50 µl of mineral oil, and cycled in a Perkin Elmer Cetus Thermal Cycler according to the following file: (1) step to 98° C.—hold 50 seconds; (2) step to 55° C.—hold 10 seconds; (3) ramp to 75° C. over 4 minutes; (4) step to 98° C. The file was repeated for a total of 30 cycles.

One-fifth (20 µl) of the amplification product was purified on a 1.5% agarose gel, and the approximately 670 bp fragment was eluted, concentrated, and digested with BglII and EcoRI as above.

These amplification reactions yielded a 667 bp fragment and a 230 bp fragment, which was a subfragment of the 667 bp fragment. These fragments proved useful in obtaining the complete coding sequence for the Tma DNA polymerase I gene, as described in the following example.

EXAMPLE 3

Cloning the *Thermotoga maritima* (Tma) DNA Polymerase I Gene

This Example describes the strategy and methodology for cloning the Tma DNA polymerase I (Tma Pol I) gene of *Thermotoga maritima*.

The DNA sequences of the PCR products generated with primers DG164–167 and DG160–163 (230 bp) and DG154, 155 and DG160–163 (667 bp) contain an XmaI restriction site recognition sequence, 5'CCCGGG. Oligonucleotides were designed to hybridize to sequences upstream and downstream of the XmaI site. DG224 is a 21 mer, homologous to the PCR products 59–79 bp 3'-distal to the XmaI site. DG225 is a 22 mer, homologous to the PCR products from the XmaI site to 21 bp upstream (5') of the XmaI site. The sequence of DG224 and of DG225 is shown below CK is G or T).

| DG224 | SEQ ID NO: 12 | 5'ACAGCAGCKGATATAATAAAG |
| DG225 | SEQ ID NO: 13 | 5'GCCATGAGCTGTGGTATGTCTC |

DG224 and DG225 were labelled by tailing with biotin-dUTP and terminal transferase in reactions designed to add approximately 8 biotin-dUMP residues to the 3'-end of oligonucleotides. These labelled oligonucleotides were used as probes in Southern blot analyses of restriction digests of genomic Tma DNA. A preliminary restriction map was generated based on the Southern analysis results, and the DNA sequences of the PCR products that were generated as described in Example 2.

The preliminary map showed that the entire Tma DNA polymerase gene is contained in two XmaI fragments. Most of the gene, including the 5'-end, resides on an approximately 2.6 kb XmaI fragment. The remainder of the gene (and the 3'-end) resides on an approximately 4.2 kb XmaI fragment. The two XmaI fragments containing the entire Tma DNA polymerase gene were cloned into plasmid pBS13+ (also called pBSM13+) as described below.

About 40 micrograms of Tma genomic DNA were digested to completion with XmaI. The XmaI digest was size-fractionated via electroelution. Slot blot analyses of a small portion of each fraction, using $\gamma$-$^{32}$P-ATP-kinased DG224 and DG225 probes, identified the tractions containing the 4.2 kb 3'-fragment (hybridizing with DG224) and the 2.6 kb 5'-fragment (hybridizing with DG225). Fractions were concentrated via ethanol precipitation and then ligated with XmaI-digested pBS13+ (Stratagene). Ampicillin-resistant transformants were selected on nitrocellulose filters and the filters probed with $\gamma$-$^{32}$P-ATP-kinased DG224 or DG225 probe as appropriate. Plasmid DNA was isolated from colonies that hybridized with probe. Restriction analysis was performed to confirm that fragments were as expected and to determine orientation of fragments relative to the pBS13+ vector.

DNA sequence analysis of the cloned fragments was performed using the "universal" and "reverse" sequencing primers (which prime in the vector, outside the restriction site polylinker region). In addition, for 5'-clones, the primers used to determine the DNA sequence of the DG154–155/ DG160–163 667 bp PCR clone were employed. Preliminary DNA sequence analysis confirmed that the desired DNA fragments containing the Tma DNA polymerase gene had been cloned.

From the preliminary DNA sequence, further sequencing primers were designed to obtain DNA sequence of more internal regions of the fragments. In addition, to facilitate DNA sequence analysis, several deletions of the two XmaI fragments were made. For both orientations of the 2.6 kb 5'-fragment, EcoRI, SacI, and XbaI digests were each diluted and ligated under conditions that favored intramolecular ligation, thus deleting DNA between the vector EcoRI, SacI, and XbaI sites and the corresponding sites in the Tma XmaI fragment. Such internal deletions allow ready DNA sequence analysis using the "universal" or "reverse" sequencing primers.

Similarly, a deletion of the 4.2 kb 3'-fragment was made, fusing the BamHI site of the vector with the BglII site approximately 650 bp from the Tma Pol I internal XmaI site in that clone (BamHI and BglII have identical GATC cohesive ends that ligate readily with one another). This deletion allows for DNA sequence analysis of the 3'-end of the Tma Pol I gene.

Restriction site analysis reveals that both the 2.6 kb 5'-fragment and the 4.2 kb 3'-fragment lack NcoI, NdeI, and AseI restriction sites. Knowing the ATG start and coding sequence of the Tma Pol I gene, one can design oligonucleotides that will alter the DNA sequence at the ATG start to include an NcoI, NdeI, or AseI restriction site via oligonucleotide site-directed mutagenesis. In addition, the mutagenic oligonucleotides can be designed such that a deletion of sequences between the lac promoter in the pBS13+ vector and the beginning of the Tma Pol I gene is made concurrent with the inclusion of an NdeI or AseI recognition sequence at the ATG start.

The deletion of sequences between the lac promoter in the vector and start of the Tma Pol I gene would also eliminate the XmaI restriction site in the deleted region, thus making it convenient to assemble the entire coding sequence in an expression plasmid using conventional skill in the art (see, e.g., synthesis protocols for pDG174–pDG181 in copending Ser. No. 455,967, filed Dec. 22, 1989, incorporated herein by reference, and Example 5).

EXAMPLE 4

PCR With Tma DNA Polymerase

About 1.25 units of the Tma DNA polymerase purified in Example 1 is used to amplify rRNA sequences from Tth genomic DNA. The reaction volume is 50 μl, and the reaction mixture contains 50 pmol of primer DG73, $10^5$ to $10^6$ copies of the Tth genome (~$2\times10^5$ copies of genome/ng DNA), 50 pmol of primer DG74, 200 μM of each dNTP, 2 mM MgCl$_2$, 10 mM Tris-HCl, pH 8.3, 50 mM KCl, and 100 μg/ml gelatin (optionally, gelatin may be omitted).

The reaction is carried out on a Perkin-Elmer Cetus Instruments DNA Thermal Cycler. Twenty to thirty cycles of 96° C. for 15 seconds; 50° C. for 30 seconds, and 75° C. for 30 seconds are carried out. At 20 cycles, the amplification product (160 bp in size) can be faintly seen on an ethidium bromide stained gel, and at 30 cycles, the product is readily visible (under UV light) on the ethidium bromide stained gel.

The PCR may yield fewer non-specific products if fewer units of Tma DNA polymerase are used (i.e., 0.31 units/50 μl reaction). Furthermore, the addition of a non-ionic detergent, such as laureth-12, to the reaction mixture to a final concentration of about 0.5% to 1% can improve the yield of PCR product.

Primers DG73 and DG74 are shown below:

| DG73 | SEQ ID NO: 14 | 5'TACGTTCCCGGGCCTTGTAC |
|---|---|---|
| DG74 | SEQ ID NO: 15 | 5'AGGAGGTGATCCAACCGCA |

EXAMPLE 5

Recombinant Expression Vectors for Tma DNA Polymerase

A. Mutagenesis of the 5' and 3' Ends of the Tma Pol I Gene

The 5' end of the Tma gene in vector pBS:Tma7-1 (ATCC No. 68471, later renamed pTma01) was mutagenized with oligonucleotides DG240 and DG244 via oligonucleotide site-directed mutagenesis. Plasmid pBS:Tma7-1 consists of the 2.6 kb 5' XmaI fragment cloned into vector pBS13+. Resultant mutants from both mutageneses had deletions between the ATG of β-galactosidase in the pBS+ vector and the ATG of Tma Pol I so that the Tma coding sequence was positioned for expression utilizing the vector lac promoter, operator, and ribosome binding site (RBS). Both sets of mutants also had alterations in the second and sixth codons for Tma Pol I to be more compatible with the codon usage of E. coli without changing the amino acid sequence of the encoded protein. In addition, DG240 placed an NdeI restriction site at the ATG start of the coding sequence (5'CATATG), and DG244 placed an NcoI restriction site at the ATG start of the coding sequence (5'CCATGG). DG240 mutant candidate colonies were screened with [$\gamma^{32}$P]-labelled oligonucleotide DG241, and DG244 mutant candidate colonies were screened with [$\gamma^{32}$P]-labelled oligonucleotide DG245. Plasmid DNA was isolated from colonies that hybridized with the appropriate probes, and mutations were confirmed via restriction analysis and DNA sequence analysis. The DG240 mutant was named pTma5'Nde#3 and later renamed pTma06. The DG244 mutant was named pTma5'Nco#9 and later renamed pTma07.

The 3'-end of the Tma Pol I gene was mutagenized in pBSTma3'11-1 Bam/Bgl (ATCC No. 68472, later renamed pTma04) with mutagenic oligonucleotide DG238. Plasmid pBSTma3'11-1 Bam/Bgl was constructed as described in Example 3 by cloning the 4.2 kb 3' XmaI fragment into pBS13+, digesting the resulting plasmid with BamHI and BglII, and circularizing by ligation the large fragment from the digestion. DG238 inserts EcoRV and BamHI sites immediately downstream of the TGA stop codon. Mutant colony candidates were identified with [$\gamma^{32}$P]-labelled oligonucleotide DG239. Plasmid DNA isolated from positive colonies was screened for appropriate restriction digest patterns, and the DNA sequence was confirmed. One correct plasmid obtained was designated as pTma3'mut#1 and later renamed pTma05.

B. Assembling the Full-Length Gene in a lac Promoter Vector

For purposes of studying low level expression of Tma Pol I in E. coli and possible complementation of E. coli polymerase mutants by Tma Pol I (where high level expression might kill the cell, but where low level expression might rescue or complement), the Tma Pol I gene was assembled in the pBS13+ cloning vector. An ~300 bp XmaI to EcoRV fragment from pTma3'mut#1 was isolated and purified, following agarose gel electrophoresis and ethidium bromide staining, by excising an agarose gel slice containing the ~300 bp fragment and freezing in a Costar spinex filter unit. Upon thawing, the unit was spun in a microfuge, and the liquid containing the DNA fragment was collected. After ethanol precipitation, the fragment was ligated with each of the two 5'-mutated vectors, pTma5'Nde#3 and pTma5'Nco#9, which had each been digested with Asp718, repaired with Klenow and all 4 dNTPs (the reaction conditions are 56 mM Tris-Cl, pH 8.0, 56 mM NaCl, 6 mM MgCl$_2$, 6 mM DTT, 5 μM dNTPs, and 11 units of Klenow at 37° C. for 15 minutes; then inactivate at 75° C. for 10 minutes), and then further digested with XmaI.

The ligation was carried out in two steps. To ligate the XmaI sticky ends, the conditions were 20 μg/ml total DNA, 20 mM Tris-Cl, pH 7.4, 50 mM NaCl, 10 mM MgCl$_2$, 40 μM ATP, and 0.2 Weiss units T4 DNA ligase per 20 μl reaction at 0° C. overnight. To ligate Asp718-digested, Klenow repaired blunt ends with EcoRV-digested blunt ends, the first ligations are diluted 4 to 5 fold and incubated at 15° C. in the same ligation buffer, except 1 mM ATP and 10 Weiss units of T4 DNA ligase are used per 20 μl reaction. Ligations were transformed into DG101 host cells. Candidates were screened for appropriate restriction sites, and the DNA sequences around the cloning sites was confirmed. The desired plasmids were designated pTma08 (NdeI site at ATG) and pTma09 (NcoI site at ATG).

C. Assembling the Full-Length Gene in P$_L$ Expression Vectors

The following table describes P$_L$ promoter expression vectors used for assembling and expressing full-length Tma Pol I under the control of λ P$_L$ promoter.

| Vector | Site at ATG | RBS* | AsuII+/−** | Oligonucleotide Duplexes Cloned into pDG160 or pDG161 | Amp/Tet*** |
|---|---|---|---|---|---|
| pDG174 | NdeI | T7 | − | DG106/DG107 | Amp |
| pDG178 | NdeI | N  | − | DG110/DG111 | Amp |
| pDG182 | NcoI | T7 | + | FL42/FL43 | Amp |
| pDG184 | NcoI | N  | + | FL44/FL45 | Amp |
| pDG185 | NcoI | N  | + | FL44/FL45 | Tet |

*RBS — Phage T7 gene 10 or lambda gene N ribosome bind site.
**AsuII sites destroyed by digestion with Csp45I, repair with Klenow, and ligation of the repaired ends.
***Antibiotic resistance determinant ampicillin or tetracycline.

The five vectors in the table are derivatives of plasmid pDG160, if ampicillin resistant, or pDG161, if tetracycline resistant. Plasmids pDG160 and pDG161 and the scheme for constructing vectors similar to the pDG vectors shown in the table are described in Ser. No. 455,967, filed Dec. 22, 1989, incorporated herein by reference. The vectors confer ampicillin or tetracycline resistance and all contain the δ-toxin positive retroregulator from *Bacillus thuringiensis* and the same point mutations in the RNA II gene that render the plasmids temperature sensitive for copy number.

The probes and oligonucleotides described in the Table are shown below.

of the methionine (ATG) codons in the coding sequence other than the 5'-ATG. The monomeric pTma12-1 plasmid produces, upon heat induction, predominantly a biologically active thermostable DNA polymerase lacking amino acids 1 through 139 of native Tma DNA polymerase. This approximately 86 kDa protein is the result of translation initiation at the methionine codon at position 140 of the Tma coding sequence and is called MET140.

In shake flask studies under the appropriate conditions (heat induction at 34° C. or 36° C., but not 38° C.), the multimeric pTma12-3 expression vector yielded a significant level of "full length" Tma DNA polymerase

| | | |
|---|---|---|
| DG240 | SEQ ID NO: 16 | |
| 5'CCATCAAAAAGAAATAGTCTAGCCATATGTGTTTCCTGTGTGAAATTG | | |
| DG241 | SEQ ID NO: 17 | 5'AAACACATATGGCTAGAC |
| DG244 | SEQ ID NO: 18 | |
| 5'CCATCAAAAAGAAATAGTCTAGCCATGGTTGTTTCCTGTGTGAAATTG | | |
| DG245 | SEQ ID NO: 19 | 5'AAACAACCATGGCTAGAC |
| DG238 | SEQ ID NO: 20 | |
| 5'GCAAAACATGGTCGTGATATCGGATCCGGAGGTGTTATCTGTGG | | |
| DG239 | SEQ ID NO: 21 | 5'CCGATATCACGACCATG |
| DG106 | SEQ ID NO: 22 | 5'CCGGAAGAAGGAGATATACATATGAGCT |
| DG107 | SEQ ID NO: 23 | 5'CATATGTATATCTCCTTCTT |
| DG110 | SEQ ID NO: 24 | 5'CCGGAGGAGAAAACATATGAGCT |
| DG111 | SEQ ID NO: 25 | 5'CATATGTTTTCTCCT |
| FL42  | SEQ ID NO: 26 | 5'CCGGAAGAAGGAGAAAATACCATGGGCCCGGTAC |
| FL43  | SEQ ID NO: 27 | 5'CGGGCCCATGGTATTTTCTCCTTCTT |
| FL44  | SEQ ID NO: 28 | 5'CCGGAGGAGAAAATCCATGGGCCCGGTAC |
| FL45  | SEQ ID NO: 29 | 5'CGGGCCCATGGATTTTCTCCT |

A three-fragment ligation was used to assemble the Tma Pol I gene in the vectors. The vectors are digested with SmaI and either NdeI (pDG174, pDG178) or NcoI (pDG182, pDG184, pDG185). The 5' end of the Tma Pol I gene is from pTma5'Nde#3 digested with NdeI and XmaI or pTma5'Nco#9 digested with NcoI and XmaI. The 3' end of the gene is from pTma3'mut#1 digested with XmaI and EcoRV and the ~300 bp fragment purified as described above.

The plasmid pDG182 shown in the Table and the scheme above were used to construct expression vector pTma13. The plasmid pDG184 and the scheme above were used to construct expression vectors pTma12-1 and pTma12-3. Plasmid pTma12-3 differs from pTma12-1 in that pTma12-3 is a dimer of pTma12-1 produced during the same ligation/transformation protocol. The plasmid pDG185 and the scheme shown above were used to construct expression vector pTMa11.

Even though a vector may contain the entire polymerase coding sequence, a shortened form of the enzyme can be expressed either exclusively or in combination with a full length polymerase. These shortened forms of Tma DNA polymerase result from translation initiation occurring at one (approximately 97 kDa by SDS-PAGE) and a smaller amount of the shortened (approximately 86 kDa) form resulting from translation initiation at Met 140. Amino-acid sequencing of the full length Tma DNA polymerase indicated that the amino-terminal methionine was removed and the second-position alanine was present at the N-terminus.

Recombinant Tma DNA Polymerase was purified from *E. coli* strain DG116 containing plasmid pTma12-3. The seed flask for a 10 L fermentation contained tryptone (20 g/l), yeast extract (10 g/l), NaCl (10 g/l), ampicillin (100 mg/l), and thiamine (10 mg/l). The seed flask was innoculated with a colony from an agar plate (a frozen glycerol culture can be used). The seed flask was grown at 30° C. to between 0.5 to 2.0 O.D. ($A_{680}$). The volume of seed culture inoculated into the fermentor is calculated such that the bacterial concentration is 0.5 mg dry weight/liter. The 12.5 liter growth medium contained 60 mM $K_2HPO_4$, 16 mM $NaNH_4HPO_4$, 10 mM citric acid, and 1 mM $MgSO_4$. The following sterile components were added: 2 g/l glucose, 10 mg/l thiamine, 2.5 g/l casamino acids, 100 mg/l ampicillin, and 100 mg/l methicillin. Foaming was controlled by the addition of propylene glycol as necessary, as an antifoaming agent. Airflow was maintained at 2 l/min.

The fermentor was inoculated as described above, and the culture was grown at 30° C. for 4.5 hours to a cell density ($A_{680}$) of 0.7. The growth temperature was shifted to 35° C. to induce the synthesis of recombinant Tma DNA polymerase. The temperature shift increases the copy number of the pTma12-3 plasmid and simultaneously derepresses the lambda $P_L$ promoter controlling transcription of the modified Tma DNA polymerase gene through inactivation of the temperature-sensitive cI repressor encoded by the defective prophage lysogen in the host. The cells were grown for 21 hours to an optical density of 4 ($A_{680}$) and harvested by centrifugation. The resulting cell paste was stored at −70° C.

Recombinant Tma DNA polymerase is purified as in Example 6, below. Briefly, cells are thawed in 1 volume of TE buffer (50 mM Tris-Cl, pH 7.5, and 1.0 mM EDTA with 1 mM DTT), and protease inhibitors are added (PMSF to 2.4 mM, leupeptin to 1 µg/ml, and TLCK to 0.2 mM). The cells are lysed in an Aminco french pressure cell at 20,000 psi and sonicated to reduce viscosity. The sonicate is diluted with TE buffer and protease inhibitors to 5.5×wet weight cell mass (Fraction I), adjusted to 0.3M ammonium sulfate, and brought rapidly to 75° C. and maintained at 75° C. for 15 min. The heat-treated supernatant is chilled rapidly to 0° C., and the *E. coli* cell membranes and dentaured proteins are removed following centrifugation at 20,000×G for 30 min. The supernatant containing Tma DNA polymerase (Fraction II) is saved. The level of Polymin P necessary to precipitate >95% of the nucleic acids is determined by trial precipitation (usually in the range of 0.6 to 1% w/v). The desired amount of Polymin P is added slowly with rapid stirring at 0° C. for 30 min. and the suspension centrifuged at 20,000×G for 30 min. to remove the precipitated nucleic acids. The supernatant (Fraction III) containing the Tma DNA polymerase is saved.

Fraction III is applied to a phenyl separose column that has been equilibrated in 50 mM Tris-Cl, pH 7.5, 0.3M ammonium sulfate, 10 mM EDTA, and 1 mM DTT. The column is washed with 2 to 4 column volumes of the same buffer ($A_{280}$ to baseline), and then 1 to 2 column volumes of TE buffer containing 100 mM KCl to remove most contaminating *E. coli* proteins. Tma DNA polymerase is then eluted from the column with buffer containing 50 mM Tris-Cl, pH 7.5, 2M urea, 20% (w/v) ethylene glycol, 10 mM EDTA, and 1 mM DTT, and fractions containing DNA polymerase activity are pooled (Fraction IV).

Final purification of recombinant Tma DNA polymerase is achieved using heparin sepharose chromatography (as for native or MET284 recombinant DNA polymerase), anion exchange chromatography, or affigel blue chromatography. Recombinant Tma DNA polymerase may be diafiltered into 2.5×storage buffer, combined with 1.5 volumes of sterile 80% (w/v) glycerol, and stored at −20° C.

EXAMPLE 6

Expression of a Truncated Tma Polymerase MET284

As noted above, expression plasmids containing the complete Tma gene coding sequence expressed either a full length polymerase resulting from translation initiation at the start codon or a shortened polymerase resulting from translation initiation occurring at the methionine codon at position 140. A third methionine codon that can act as a translation initiation site occurs at position 284 of the Tma gene coding sequence. Plasmids that express a DNA polymerase lacking amino acids 1 through 283 of native Tma DNA polymerase were constructed by introducing deleting corresponding regions of the Tma coding sequence.

Plasmid pTma12-1 was digested with BspHI (nucleotide position 848) and HindIII (nucleotide position 2629). A 1781 base pair fragment was isolated by agarose gel purification. To separate the agarose from the DNA, a gel slice containing the desired fragment was frozen at −20° C. in a Costar spinex filter unit. After thawing at room temperature, the unit was spun in a microfuge. The filtrate containing the DNA was concentrated in a Speed Vac concentrator, and the DNA was precipitated with ethanol.

The isolated fragment was cloned into plasmid pTma12-1 digested with NcoI and HindIII. Because NcoI digestion leaves the same cohesive end sequence as digestion with BspHI, the 1781 base pair fragment has the same cohesive ends as the full length fragment excised from plasmid pTma12-1 by digestion with NcoI and HindIII. The ligation of the isolated fragment with the digested plasmid results in a fragment switch and was used to create a plasmid designated pTma14.

Plasmid pTma15 was similarly constructed by cloning the same isolated fragment into pTma13. As with pTma14, pTma15 drives expression of a polymerase that lacks amino acids 1 through 283 of native Tma DNA polymerase; translation initiates at the methionine codon at position 284 of the native coding sequence.

Both the pTma14 and pTma15 expression plasmids expressed at a high level a biologically active thermostable DNA polymerase of molecular weight of about 70 kDa; plasmid pTma15 expressed polymerase at a higher level than did pTma14. Based on similarities with *E. coli* Pol I Klenow fragment, such as conservation of amino acid sequence motifs in all three domains that are critical for 3'–5' exonuclease activity, distance from the amino terminus to the first domain critical for exonuclease activity, and length of the expressed protein, the shortened form (MET284) of Tma polymerase should possess 3'–5' exonuclease and proof-reading activity but lack 5'–3' exonuclease activity. However, initial SDS activity gel assays and solution assays for 3'–5' exonuclease activity suggested significant attenuation in the proof-reading activity of the polymerase expressed by *E. coli* host cells harboring plasmid pTma15.

MET284 Tma DNA Polymerase was purified from *E. coli* strain DG116 containing plasmid pTma15. The seed flask for a 10 L fermentation contained tryptone (20 g/l), yeast extract (10 g/l), NaCl (10 g/l), glucose (10 g/l), ampicillin (50 mg/l), and thiamine (10 mg/l). The seed flask was innoculated with a colony from an agar plate (a frozen glycerol culture can be used). The seed flask was grown at 30° C. to between 0.5 to 2.0 O.D. ($A_{680}$). The volume of seed culture inoculated into the fermentor is calculated such that the bacterial concentration is 0.5 mg dry weight/liter. The 10 liter growth medium contained 25 mM $KH_2PO_4$, 10 mM $(NH_4)_2SO_4$, 4 mM sodium citrate, 0.4 mM $FeCl_3$, 0.04 mM $ZnCl_2$, 0.03 mM $CoCl_2$, 0.03 mM $CuCl_2$, and 0.03 mM $H_3BO_3$. The following sterile components were added: 4 mM $MgSO_4$, 20 g/l glucose, 20 mg/l thiamine, and 50 mg/l ampicillin. The pH was adjusted to 6.8 with NaOH and controlled during the fermentation by added NH$_4$OH. Glucose was continually added by coupling to NH$_4$OH addition. Foaming was controlled by the addition of propylene glycol as necessary, as an antifoaming agent. Dissolved oxygen concentration was maintained at 40%.

The fermentor was inoculated as described above, and the culture was grown at 30° C. to a cell density of 0.5 to 1.0×10$^{10}$ cells/ml (optical density [A$_{680}$] of 15). The growth temperature was shifted to 38° C. to induce the synthesis of MET284 Tma DNA polymerase. The temperature shift increases the copy number of the pTma15 plasmid and simultaneously derepresses the lambda P$_L$ promoter controlling transcription of the modified Tma DNA polymerase gene through inactivation of the temperature-sensitive cI repressor encoded by the defective prophage lysogen in the host.

The cells were grown for 6 hours to an optical density of 37 (A$_{680}$) and harvested by centrifugation. The cell mass (ca. 95 g/l) was resuspended in an equivalent volume of buffer containing 50 mM Tris-Cl, pH 7.6, 20 mM EDTA and 20% (w/v) glycerol. The suspension was slowly dripped into liquid nitrogen to freeze the suspension as "beads" or small pellets. The frozen cells were stored at −70° C.

To 200 g of frozen beads (containing 100 g wet weight cell) were added 100 ml of 1×TE (50 mM Tris-Cl, pH 7.5, 10 mM EDTA) and DTT to 0.3 mM, PMSF to 2.4 mM, leupeptin to 1 µg/ml and TLCK (a protease inhibitor) to 0.2 mM. The sample was thawed on ice and uniformly resuspended in a blender at low speed. The cell suspension was lysed in an Aminco french pressure cell at 20,000 psi. To reduce viscosity, the lysed cell sample was sonicated 4 times for 3 min. each at 50% duty cycle and 70% output. The sonicate was adjusted to 550 ml with 1×TE containing 1 mM DTT, 2.4 mM PMSF, 1 µg/ml leupeptin and 0.2 mM TLCK (Fraction I). After addition of ammonium sulfate to 0.3M, the crude lysate was rapidly brought to 75° C. in a boiling water bath and transferred to a 75° C. water bath for 15 min. to denature and inactivate E. coli host proteins. The heat-treated sample was chilled rapidly to 0° C. and incubated on ice for 20 min. Precipitated proteins and cell membranes were removed by centrifugation at 20,000×G for 30 min. at 5° C. and the supernatant (Fraction II) saved.

The heat-treated supernatant (Fraction II) was treated with polyethyleneimine (PEI) to remove most of the DNA and RNA. Polymin P (34.96 ml of 10% [w/v], pH 7.5) was slowly added to 437 ml of Fraction II at 0° C. while stirring rapidly. After 30 min. at 0° C., the sample was centrifuged at 20,000×G for 30 min. The supernatant (Fraction III) was applied at 80 ml/hr to a 100 ml phenylseparose column (3.2×12.5 cm) that had been equilibrated in 50 mM Tris-Cl, pH 7.5, 0.3M ammonium sulfate, 10 mM EDTA, and 1 mM DTT. The column was washed with about 200 ml of the same buffer (A$_{280}$ to baseline) and then with 150 ml of 50 mM Tris-Cl, pH 7.5, 100 mM KCl, 10 mM EDTA and 1 mM DTT. The MET284 Tma DNA polymerase was then eluted from the column with buffer containing 50 mM Tris-Cl, pH 7.5, 2M urea, 20% (w/v) ethylene glycol, 10 mM EDTA, and 1 mM DTT, and fractions containing DNA polymerase activity were pooled (Fraction IV).

Fraction IV is adjusted to a conductivity equivalent to 50 mM KCl in 50 mM Tris-Cl, pH 7.5, 1 mM EDTA, and 1 mM DTT. The sample was applied (at 9 ml/hr) to a 15 ml heparin-sepharose column that had been equilibrated in the same buffer. The column was washed with the same buffer at ca. 14 ml/hr (3.5 column volumes) and eluted with a 150 ml 0.05 to 0.5M KCl gradient in the same buffer. The DNA polymerase activity eluted between 0.11–0.22M KCl. Fractions containing the pTma15 encoded modifed Tma DNA polymerase are pooled, concentrated, and diafiltered against 2.5×storage buffer (50 mM Tris-Cl, pH 8.0, 250 mM KCl, 0.25 mM EDTA, 2.5 mM DTT, and 0.5% Tween 20), subsequently mixed with 1.5 volumes of sterile 80% (w/v) glycerol, and stored at −20° C. Optionally, the heparin sepharose-eluted DNA polymerase or the phenyl sepharose-eluted DNA polymerase can be dialyzed or adjusted to a conductivity equivalent to 50 mM KCl in 50 mM Tris-Cl, pH 7.5, 1 mM DTT, 1 mM EDTA, and 0.2% Tween 20 and applied (1 mg protein/ml resin) to an affigel blue column that has been equilibrated in the same buffer. The column is washed with three to five column volumes of the same buffer and eluted with a 10 column volume KCl gradient (0.05 to 0.8M) in the same buffer. Fractions containing DNA polymerase activity (eluting between 0.25 and 0.4M KCl) are pooled, concentrated, diafiltered, and stored as above.

The relative thermoresistance of various DNA polymerases has been compared. At 97.5° C. the half-life of native Tma DNA polymerase is more than twice the half-life of either native or recombinant Taq DNA (i.e., AmpliTaq®) DNA polymerase. Surprisingly, the half-life at 97.5° C. of MET284 Tma DNA polymerase is 2.5 to 3 times longer than the half-life of native Tma DNA polymerase.

PCR tubes containing 10 mM Tris-Cl, pH 8.3, and 1.5 mM MgCl$_2$ (for Taq or native Tma DNA polymerase) or 3 mM MgCl$_2$ (for MET284 Tma DNA polymerase), 50 mM KCl (for Taq, native Tma and MET284 Tma DNA polymerases) or no KCl (for MET284 Tma DNA polymerase), 0.5 µM each of primers PCR01 and PCR02, 1 ng of lambda template DNA, 200 µM of each dNTP except dCTP, and 4 units of each enzyme were incubated at 97.5° C. in a large water bath for times ranging from 0 to 60 min. Samples were withdrawn with time, stored at 0° C., and 5 µl assayed at 75° C. for 10 min. in a standard activity assay for residual activity.

Taq DNA polymerase had a half-life of about 10 min. at 97.5° C., while native Tma DNA polymerase had a half-life of about 21 to 22 min. at 97.5° C. Surprisingly, the MET284 form of Tma DNA polymerase had a significanlty longer half-life (50 to 55 min.) than either Taq or native Tma DNA polymerase. The improved thermoresistance of MET284 Tma DNA polymerase will find applications in PCR, particularly where G+C-rich targets are difficult to amplify because the strand-separation temperature required for complete denaturation of target and PCR product sequences leads to enzyme inactivation.

PCR tubes containing 50 µl of 10 mM Tris-Cl, pH 8.3, 3 mM MgCl$_2$, 200 µM of each dNTP, 0.5 ng bacteriophage lambda DNA, 0.5 µM of primer PCR01, 4 units of MET284 Tma DNA polymerase, and 0.5 µM of primer PCR02 or PL10 were cycled for 25 cycles using T$_{den}$ of 96° C. for 1 min. and T$_{anneal-extend}$ of 60° C. for 2 min. Lambda DNA template, deoxynucleotide stock solutions, and primers PCR01 and PCR02 were pan of the PECI GeneAmp® kit.

Primer PL10 has the sequence: (SEQ ID NO. 45) 5'-GGCGTACCTTTGTCTCACGGGCAAC-3' and is complementary to bacteriophage lambda nucleotides 8106–8130.

The primers PCR01 and PCR02 amplify a 500 bp product from lambda. The primer pair PCR01 and PL10 amplify a 1 kb product from lambda. After amplification with the respective primer sets, 5 µl aliquots were subjected to agarose gel electrophoresis and the specific intended product bands visualized with ethidium bromide staining. Abundant levels of product were generated with both primer sets, showing that MET284 Tma DNA polymerase successfully amplified the intended target sequence.

EXAMPLE 7

Expression of Truncated Tma Polymerase

As noted above, host ells transformed with plasmids that contain the complete Tma DNA polymerase gene coding sequence express a shortened form (MET140) of Tma polymerase either exclusively or along with the full length polymerase. Mutations can be made to control which form of the polymerase is expressed. To enhance the exclusive expression of the MET140 form of the polymerase, the coding region corresponding to amino acids through 139 were deleted from the expression vector. The protocol for constructing such a deletion is similar to the construction described in Example 6: a shortened gene fragment is excised and then reinserted into a vector from which a full length fragment has been excised. However, the shortened fragment can be obtained as a PCR amplification product rather than purified from a restriction digest. This methodology allows a new upstream restriction site (or other sequences) to be incorporated where useful.

To delete the region up to the methionine codon at position 140, an SphI site was introduced into pTma12-1 and pTma13 using PCR. A forward primer (FL63) was designed to introduce the SphI site just upstream of the methionine codon at position 140. The reverse primer (FL69) was chosen to include an XbaI at position 624. Plasmid pTma12-1 linearized with SmaI was used as the PCR template, yielding a 225 bp PCR product.

Before digestion, the PCR product was treated with 50 µg/ml of Proteinase K in PCR reaction mix plus 0.5% SDS and 5 mM EDTA. After incubating for 30 minutes at 37° C., the Proteinase K was heat inactivated at 68° C. for 10 minutes. This procedure eliminated any Taq polymerase bound to the product that could inhibit subsequent restriction digests. The buffer was changed to a TE buffer, and the excess PCR primers were removed with a Centricon 100 microconcentrator.

The amplified fragment was digested with SphI, then treated with Klenow to create a blunt end at the SphI-cleaved end, and finally digested with XbaI. The resulting fragment was ligated with plasmid pTma13 (pTma12-1 would have been suitable) that had been digested with NcoI, repaired with Klenow, and then digested with XbaI. The ligation yielded an in-frame coding sequence with the region between the initial NcoI site (upstream of the first methionine codon of the coding sequence) and the introduced SphI site (upstream of the methionine codon at position 140) deleted. The resulting expression vector was designated pTma 16.

The primers used in this example are given below and in the Sequence Listing section.

| Primer | SEQ ID NO: | Sequence |
| --- | --- | --- |
| FL63 | SEQ ID NO: 30 | 5'GATAAAGGCATGCTTCAGCTTGTGAACG |
| FL69 | SEQ ID NO: 31 | 5'TGTACTTCTCTAGAAGCTGAACAGCAG |

EXAMPLE 8

Elimination of Undesired RBS in MET140 Expression Vectors

Reduced expression of the MET140 form of Tma DNA polymerase can be achieved by eliminating the ribosome binding site (RBS) upstream of the methionine codon at position 140. The RBS was be eliminated via oligonucleotide site-directed mutagenesis without changing the amino acid sequence. Taking advantage of the redundancy of the genetic code, one can make changes in the third position of codons to alter the nucleic acid sequence, thereby eliminating the RBS, without changing the amino acid sequence of the encoded protein.

A mutagenic primer (FL64) containing the modified sequence was synthesized and phosphorylated. Single-stranded pTma09 (a full length clone having an NcoI site) was prepared by coinfecting with the helper phage R408, commercially available from Stratagene. A "gapped duplex" of single stranded pTma09 and the large fragment from the PvuII digestion of pBS13+ was created by mixing the two plasmids, heating to boiling for 2 minutes, and cooling to 65° C. for 5 minutes. The phosphorylated primer was then annealed with the "gapped duplex" by mixing, heating to 80° C. for 2 minutes, and then cooling slowly to room temperature. The remaining gaps were filled by extension with Klenow and the fragments ligated with T4 DNA ligase, both reactions taking place in 200 µM of each dNTP and 40 µM ATP in standard salts at 37° C. for 30 minutes.

The resulting circular fragment was transformed into DG101 host cells by plate transformations on nitrocellulose filters. Duplicate filters were made and the presence of the correct plasmid was detected by probing with a $\gamma^{32}$P-phosphorylated probe (FL65). The vector that resulted was designated pTma19.

The RBS minus portion from pTma19 was cloned into pTma12-1 via an NcoI/XbaI fragment switch. Plasmid pTma19 was digested with NcoI and XbaI, and the 620 bp fragment was purified by gel electrophoresis, as in Example 7, above. Plasmid pTma12-1 was digested with NcoI, XbaI, and XcmI. The XcmI cleavage inactivates the RBS+ fragment for the subsequent ligation step, which is done under conditions suitable for ligating "sticky" ends (dilute ligase and 40 µM ATP). Finally, the ligation product is transformed into DG116 host cells for expression and designated pTma19-RBS.

The oligonucleotide sequences used in this example are listed below and in the Sequence Listing section.

| Oligo | SEQ ID NO: | Sequence |
|---|---|---|
| FL64 | SEQ ID NO: 32 | 5'CTGAAGCATGTCTTTGTCACCGGTTACTATGAATAT |
| FL65 | SEQ ID NO: 33 | 5'TAGTAACCGGTGACAAAG |

EXAMPLE 9

Expression of Truncated Tma DNA Polymerase MET-ASP21

To effect translation initiation at about the aspartic acid codon at position 21 of the Tma DNA polymerase gene coding sequence, a methionine codon is introduced before the codon, and the region from the initial NcoI site to this introduced methionine codon is deleted. The deletion process involves PCR with the same downstream primer described above (FL69) and with an upstream primer (FL66) designed to incorporate an NcoI site and a methionine codon to yield a 570 base pair product.

The amplified product is concentrated with a Centricon-100 microconcentrator to eliminate excess primers and buffer. The product is concentrated in a Speed Vac concentrator and then resuspended in the digestion mix. The amplified product is digested with NcoI and XbaI. Likewise, pTma12-1, pTma13, or pTma19-RBS is digested with the same two restriction enzymes, and the digested, amplified fragment is ligated with the digested expression vector. The resulting construct has a deletion from the NcoI site upstream of the start codon of the native Tma coding sequence to the new methionine codon introduced upstream of the aspartic acid codon at position 21 of the native Tma coding sequence.

Similarly, a deletion mutant can be created such that translation initiation begins at Glu74, the glutamic acid codon at position 74 of the native Tma coding sequence. An upstream primer (FL67) is designed to introduce a methionine codon and an NcoI site before Glu74. The downstream primer and cloning protocol used are as described above for the MET-ASP21 construct.

The upstream primer sequences used in this example are listed below and in the Sequence Listing section.

sion vector. The T7 Gene 10 promoter and RBS have been used to drive expression of Tma DNA polymerase from expression vector pTma17, and the T7 Gene 10 promoter and the Gene N RBS have been used to drive expression of Tma DNA polymerase from expression vector pTma18. The construction of these vectors took advantage of unique restriction sites present in pTma12-1: an AflII site upstream of the promoter, an NcoI site downstream of the RBS, and a BspEI site between the promoter and the RBS. The existing promoter was excised from pTma12-1 and replaced with a synthetic T7 Gene 10 promoter using techniques similar to those described in the previous examples.

The synthetic insert was created from two overlapping synthetic oligonucleotides. To create pTma17 (with T7 Gene 10 RBS), equal portions of FR414 and FR416 were mixed, heated to boiling, and cooled slowly to room temperature. The hybridized oligonucleotides were extended with Klenow to create a full length double stranded insert. The extended fragment was then digested with AflII and NcoI, leaving the appropriate "sticky" ends. The insert was cloned into plasmid pTma12-1 digested with AflII and NcoI. DG116 host cells were transformed with the resulting plasmid and transformants screened for the desired plasmid.

The same procedure was used in the creation of pTma18 (with Gene N RBS), except that FR414 and FR418 were used, and the extended fragment was digested with AflII and BspEI. This DNA fragment was substituted for the $P_L$ promoter in plasmid pTma12-1 that had been digested with AplII and BspEI.

Plasmids pTma17 and pTma18 are used to transform *E. coli* host cells that have been modified to contain an inducible T7 DNA polymerase gene.

The oligonucleotides used in the construction of these vectors are listed below and in the Sequence Listing section.

| Oligo | SEQ ID NO: | Sequence |
|---|---|---|
| FL66 | SEQ ID NO: 34 | 5'CTATGCCATGGATAGATCGCTTTCTACTTCC |
| FL67 | SEQ ID NO: 35 | 5'CAAGCCCATGGAAACTTACAAGGCTCAAAGA |

EXAMPLE 10

Expression Vectors With T7 Promoters

Expression efficiency can be altered by changing the promoter and/or ribosomal binding site (RBS) in an expres-

| | | |
|---|---|---|
| FR414 | SEQ ID NO: 36 | |
| 5'TCAGCTTAAGACTTCGAAATTAATACGACTCACTATAGGGAGACCACAACGGTTTCCCTC | | |
| FR416 | SEQ ID NO: 37 | |
| 5'TCGACCATGGGTATATCTCCTTCTTAAAGTTAAACAAAATTATTTCTAGAGGAAACCGTTG | | |
| FR418 | SEQ ID NO: 38 | |
| 5'TCAGTCCGGATAAACAAAATTATTTCTAGAGGGAAACCGTTG | | |

EXAMPLE 11

Translational Coupling

As described above, translational coupling can increase the efficiency of expression of a protein by coupling a short coding sequence just upstream of the initiation site of the coding sequence for the protein. Termination of translation of the upstream coding sequence leaves the ribosome in close proximity to the initiation site for the downstream coding sequence. The upstream coding sequence functions only to move the ribosome downstream to the start of the coding sequence for the desired protein.

Translationally coupled Tma expression vectors were constructed with the translation initiation signal and first ten codons of the T7 bacteriophage major capsid protein (gene 10) fused in-frame to the last six codons of E. coli TrpE placed upstream of the Tma coding region. The TGA (stop) codon for TrpE is "coupled" with the ATG (start) codon for the Tma gene, forming the sequence TGATG. A one base frame-shift is required between translation of the short coding sequence and translation of the Tma coding sequence.

In the example below, a fragment containing the T7 Gene 10-E. coli TrpE/TrpD fusion product (the last 6 codons and TGA stop codon from TrpE along with the overlapping ATG start codon from TrpD) was transferred from a pre-existing plasmid. One of ordinary skill will recognize that the T7 Gene 10-E. coli TrpE/TrpD fusion product used in the construction of the translationally coupled expression vectors can be constructed as a synthetic oligonucleotide. The sequence for the inserted fragment is listed below and in the Sequence Listing section.

The T7 Gene 10-E. coli TrpE/TrpD fusion product was amplified from plasmid pSYC1868 with primers FL48 and FL49. With primers FL51 and FL53, the 5' end of the Tma Pol I gene in pTma08 (a full length clone containing an NdeI site) was amplified from the ATG start codon to the MroI site downstream of the ATG start codon. The primers FL51 and FL49 were designed to leave overlapping regions such that the two amplified products could be annealed and extended, essentially as described in Example 10. The two amplification products were mixed, heated to 95° C., slowly cooled to room temperature to anneal, and extended with Taq polymerase.

The extended insert was amplified with primers FL48 and FL53 and then digested with XmaI and MroI. Plasmid pTma12-1 was digested with MroI and treated with calf intestine alkaline phosphatase to prevent re-ligation. The digested pTma12-1 was ligated with the insert. DG116 host cells were transformed with the resulting construct and transformants screened for the desired plasmid DNA. The resulting vector was designated pTma20.

The sequences of the oligonucleotide primers and the T7 Gene 10-E. coli TrpE/TrpD fusion product (Gene 10 insert) are listed below and in the Sequence Listing section.

| Primers | SEQ ID NO: | Sequence |
|---|---|---|
| FL48 | SEQ ID NO: 39 | 5'TCCGGACTTTAAGAAGGAGATATAC |
| FL49 | SEQ ID NO: 40 | 5'AATAGTCTAGCCATCAGAAAGTCTCCTGTGC |
| FL51 | SEQ ID NO: 41 | 5'AGACTTTCTGATGGCTAGACTATTTCTT |
| FL53 | SEQ ID NO: 42 | 5'CTGAATCAGGAGACCCGGGGTCTTTGGTC |
| Gene 10 insert | SEQ ID NO: | 5'CTTTAAGAAGGAGATATACATATGGCTAGCATGACTGGTGGACAGCAAATGCATGCACAGGAGACTTTCTGATG |

EXAMPLE 12

Arg U tRNA Expression

The pattern of codon usage differs between Thermotoga maritima and E. coli. In the Tma coding sequence, arginine is most frequently coded for by the "AGA" codon, whereas this codon is used in low frequency in E. coli host cells. The corresponding "Arg U" tRNA appears in low concentrations in E. coli. The low concentration in the host cell of Arg tRNA using the "AGA" codon may limit the translation efficiency of the Tma polymerase gene. The efficiency of translation of the Tma coding sequence within an E. coli host may be improved by increasing the concentration of this tRNA species by cloning multiple copies of the tRNA gene into the host cell using a second expression vector that contains the gene for the "Arg U" tRNA.

The Arg U tRNA gene was PCR amplified from E. coli genomic DNA using the primers DG284 and DG285. The amplification product was digested with SalI and BamHI. The ColEI compatible vector pACYC184 was digested with SalI and BamHI, and the Arg U gene fragment was subsequently ligated with the digested vector. DG101 cells were transformed, and the ligated vector was designated pARG01. Finally, DG116 host cells were co-transformed with pARG01 and pTma12-1.

The oligonucleotide primers used in this Example are listed below and in the Sequence Listing section.

| Primers | SEQ ID NO: | Sequence |
|---|---|---|
| DG284 | SEQ ID NO: 43 | 5'CGGGGATCCAAAAGCCATTGACTCAGCAAGG |
| DG285 | SEQ ID NO: 44 | 5'GGGGGTCGACGCATGCGAGGAAAATAGACG |

We claim:

1. A purified thermostable DNA polymerase I enzyme that catalyzes combination of nucleoside triphosphates to form a nucleic acid strand complementary to a nucleic acid template strand, said enzyme derived from the eubacterium *Thermotoga maritima*.

2. The enzyme of claim 1 having a molecular weight of about 97 kilodaltons as determined by SDS-page, a predicted molecular weight of about 102 kilodaltons.

3. The enzyme of claim 1 that has reverse transcriptase activity.

4. The enzyme of claim 1 that has 3'→5' exonuclease activity.

5. The enzyme of claim 1 that is in native form.

6. The enzyme of claim 2 that is in native form.

7. The enzyme of claim 1 that is in recombinant form.

8. The enzyme of claim 2 that is in recombinant form.

9. The enzyme of claim 2 that has reverse transcriptase and 3'→5' exonuclease activity.

10. The enzyme of claim 9 that is in native form.

11. The enzyme of claim 9 that is in recombinant form.

12. A method for purifying *Thermotoga maritima* DNA polymerase from *T. maritima* cells, said method comprising the steps of:

(a) preparing a crude cell extract from said cells;

(b) adjusting the ionic strength of said extract so that said polymerase dissociates from any nucleic acid in said extract;

(c) subjecting the extract to hydrophobic interaction chromatography;

(d) subjecting the extract to DNA binding protein affinity chromatography;

(e) subjecting the extract to nucleotide binding protein affinity chromatography; and (f) subjecting the extract to chromatography selected from the group consisting of anion exchange, cation exchange, and hydroxyapatite chromatography.

* * * * *

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 2682 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..2682

( x i ) SEQUENCE DESCRIPTION: SEQ ID NO:1:

```
ATG GCG AGA CTA TTT CTC TTT GAT GGA ACT GCT CTG GCC TAC AGA GCG      48
Met Ala Arg Leu Phe Leu Phe Asp Gly Thr Ala Leu Ala Tyr Arg Ala
 1               5                  10                  15

TAC TAT GCG CTC GAT AGA TCG CTT TCT ACT TCC ACC GGC ATT CCC ACA      96
Tyr Tyr Ala Leu Asp Arg Ser Leu Ser Thr Ser Thr Gly Ile Pro Thr
                20                  25                  30

AAC GCC ACA TAC GGT GTG GCG AGG ATG CTG GTG AGA TTC ATC AAA GAC     144
Asn Ala Thr Tyr Gly Val Ala Arg Met Leu Val Arg Phe Ile Lys Asp
            35                  40                  45

CAT ATC ATT GTC GGA AAA GAC TAC GTT GCT GTG GCT TTC GAC AAA AAA     192
His Ile Ile Val Gly Lys Asp Tyr Val Ala Val Ala Phe Asp Lys Lys
        50                  55                  60

GCT GCC ACC TTC AGA CAC AAG CTC CTC GAG ACT TAC AAG GCT CAA AGA     240
Ala Ala Thr Phe Arg His Lys Leu Leu Glu Thr Tyr Lys Ala Gln Arg
65                  70                  75                  80

CCA AAG ACT CCG GAT CTC CTG ATT CAG CAG CTT CCG TAC ATA AAG AAG     288
Pro Lys Thr Pro Asp Leu Leu Ile Gln Gln Leu Pro Tyr Ile Lys Lys
                85                  90                  95

CTG GTC GAA GCC CTT GGA ATG AAA GTG CTG GAG GTA GAA GGA TAC GAA     336
Leu Val Glu Ala Leu Gly Met Lys Val Leu Glu Val Glu Gly Tyr Glu
            100                 105                 110

GCG GAC GAT ATA ATT GCC ACT CTG GCT GTG AAG GGG CTT CCG CTT TTT     384
Ala Asp Asp Ile Ile Ala Thr Leu Ala Val Lys Gly Leu Pro Leu Phe
        115                 120                 125

GAT GAA ATA TTC ATA GTG ACC GGA GAT AAA GAC ATG CTT CAG CTT GTG     432
Asp Glu Ile Phe Ile Val Thr Gly Asp Lys Asp Met Leu Gln Leu Val
    130                 135                 140

AAC GAA AAG ATC AAG GTG TGG CGA ATC GTA AAA GGG ATA TCC GAT CTG     480
Asn Glu Lys Ile Lys Val Trp Arg Ile Val Lys Gly Ile Ser Asp Leu
145                 150                 155                 160

GAA CTT TAC GAT GCG CAG AAG GTG AAG GAA AAA TAC GGT GTT GAA CCC     528
Glu Leu Tyr Asp Ala Gln Lys Val Lys Glu Lys Tyr Gly Val Glu Pro
                165                 170                 175

CAG CAG ATC CCG GAT CTT CTG GCT CTA ACC GGA GAT GAA ATA GAC AAC     576
Gln Gln Ile Pro Asp Leu Leu Ala Leu Thr Gly Asp Glu Ile Asp Asn
            180                 185                 190

ATC CCC GGT GTA ACT GGG ATA GGT GAA AAG ACT GCT GTT CAG CTT CTA     624
Ile Pro Gly Val Thr Gly Ile Gly Glu Lys Thr Ala Val Gln Leu Leu
        195                 200                 205

GAG AAG TAC AAA GAC CTC GAA GAC ATA CTG AAT CAT GTT CGC GAA CTT     672
Glu Lys Tyr Lys Asp Leu Glu Asp Ile Leu Asn His Val Arg Glu Leu
    210                 215                 220
```

```
CCT CAA AAG GTG AGA AAA GCC CTG CTT CGA GAC AGA GAA AAC GCC ATT    720
Pro Gln Lys Val Arg Lys Ala Leu Leu Arg Asp Arg Glu Asn Ala Ile
225                 230                 235                 240

CTC AGC AAA AAG CTG GCG ATT CTG GAA ACA AAC GTT CCC ATT GAA ATA    768
Leu Ser Lys Lys Leu Ala Ile Leu Glu Thr Asn Val Pro Ile Glu Ile
                    245                 250                 255

AAC TGG GAA GAA CTT CGC TAC CAG GGC TAC GAC AGA GAG AAA CTC TTA    816
Asn Trp Glu Glu Leu Arg Tyr Gln Gly Tyr Asp Arg Glu Lys Leu Leu
                260                 265                 270

CCA CTT TTG AAA GAA CTG GAA TTC GCA TCC ATC ATG AAG GAA CTT CAA    864
Pro Leu Leu Lys Glu Leu Glu Phe Ala Ser Ile Met Lys Glu Leu Gln
            275                 280                 285

CTG TAC GAA GAG TCC GAA CCC GTT GGA TAC AGA ATA GTG AAA GAC CTA    912
Leu Tyr Glu Glu Ser Glu Pro Val Gly Tyr Arg Ile Val Lys Asp Leu
        290                 295                 300

GTG GAA TTT GAA AAA CTC ATA GAG AAA CTG AGA GAA TCC CCT TCG TTC    960
Val Glu Phe Glu Lys Leu Ile Glu Lys Leu Arg Glu Ser Pro Ser Phe
305                 310                 315                 320

GCC ATA GAT CTT GAG ACG TCT TCC CTC GAT CCT TTC GAC TGC GAC ATT    1008
Ala Ile Asp Leu Glu Thr Ser Ser Leu Asp Pro Phe Asp Cys Asp Ile
                    325                 330                 335

GTC GGT ATC TCT GTG TCT TTC AAA CCA AAG GAA GCG TAC TAC ATA CCA    1056
Val Gly Ile Ser Val Ser Phe Lys Pro Lys Glu Ala Tyr Tyr Ile Pro
                340                 345                 350

CTC CAT CAT AGA AAC GCC CAG AAC CTG GAC GAA AAA GAG GTT CTG AAA    1104
Leu His His Arg Asn Ala Gln Asn Leu Asp Glu Lys Glu Val Leu Lys
            355                 360                 365

AAG CTC AAA GAA ATT CTG GAG GAC CCC GGA GCA AAG ATC GTT GGT CAG    1152
Lys Leu Lys Glu Ile Leu Glu Asp Pro Gly Ala Lys Ile Val Gly Gln
        370                 375                 380

AAT TTG AAA TTC GAT TAC AAG GTG TTG ATG GTG AAG GGT GTT GAA CCT    1200
Asn Leu Lys Phe Asp Tyr Lys Val Leu Met Val Lys Gly Val Glu Pro
385                 390                 395                 400

GTT CCT CCT TAC TTC GAC ACG ATG ATA GCG GCT TAC CTT CTT GAG CCG    1248
Val Pro Pro Tyr Phe Asp Thr Met Ile Ala Ala Tyr Leu Leu Glu Pro
                    405                 410                 415

AAC GAA AAG AAG TTC AAT CTG GAC GAT CTC GCA TTG AAA TTT CTT GGA    1296
Asn Glu Lys Lys Phe Asn Leu Asp Asp Leu Ala Leu Lys Phe Leu Gly
                420                 425                 430

TAC AAA ATG ACA TCT TAC CAA GAG CTC ATG TCC TTC TCT TTT CCG CTG    1344
Tyr Lys Met Thr Ser Tyr Gln Glu Leu Met Ser Phe Ser Phe Pro Leu
            435                 440                 445

TTT GGT TTC AGT TTT GCC GAT GTT CCT GTA GAA AAA GCA GCG AAC TAC    1392
Phe Gly Phe Ser Phe Ala Asp Val Pro Val Glu Lys Ala Ala Asn Tyr
        450                 455                 460

TCC TGT GAA GAT GCA GAC ATC ACC TAC AGA CTT TAC AAG ACC CTG AGC    1440
Ser Cys Glu Asp Ala Asp Ile Thr Tyr Arg Leu Tyr Lys Thr Leu Ser
465                 470                 475                 480

TTA AAA CTC CAC GAG GCA GAT CTG GAA AAC GTG TTC TAC AAG ATA GAA    1488
Leu Lys Leu His Glu Ala Asp Leu Glu Asn Val Phe Tyr Lys Ile Glu
                    485                 490                 495

ATG CCC CTT GTG AAC GTG CTT GCA CGG ATG GAA CTG AAC GGT GTG TAT    1536
Met Pro Leu Val Asn Val Leu Ala Arg Met Glu Leu Asn Gly Val Tyr
                500                 505                 510

GTG GAC ACA GAG TTC CTG AAG AAA CTC TCA GAA GAG TAC GGA AAA AAA    1584
Val Asp Thr Glu Phe Leu Lys Lys Leu Ser Glu Glu Tyr Gly Lys Lys
            515                 520                 525

CTC GAA GAA CTG GCA GAG GAA ATA TAC AGG ATA GCT GGA GAG CCG TTC    1632
Leu Glu Glu Leu Ala Glu Glu Ile Tyr Arg Ile Ala Gly Glu Pro Phe
        530                 535                 540
```

```
AAC ATA AAC TCA CCG AAG CAG GTT TCA AGG ATC CTT TTT GAA AAA CTC  1680
Asn Ile Asn Ser Pro Lys Gln Val Ser Arg Ile Leu Phe Glu Lys Leu
545             550             555             560

GGC ATA AAA CCA CGT GGT AAA ACG ACG AAA ACG GGA GAC TAT TCA ACA  1728
Gly Ile Lys Pro Arg Gly Lys Thr Thr Lys Thr Gly Asp Tyr Ser Thr
                565             570             575

CGC ATA GAA GTC CTC GAG GAA CTT GCC GGT GAA CAC GAA ATC ATT CCT  1776
Arg Ile Glu Val Leu Glu Glu Leu Ala Gly Glu His Glu Ile Ile Pro
            580             585             590

CTG ATT CTT GAA TAC AGA AAG ATA CAG AAA TTG AAA TCA ACC TAC ATA  1824
Leu Ile Leu Glu Tyr Arg Lys Ile Gln Lys Leu Lys Ser Thr Tyr Ile
        595             600             605

GAC GCT CTT CCC AAG ATG GTC AAC CCA AAG ACC GGA AGG ATT CAT GCT  1872
Asp Ala Leu Pro Lys Met Val Asn Pro Lys Thr Gly Arg Ile His Ala
610             615             620

TCT TTC AAT CAA ACG GGG ACT GCC ACT GGA AGA CTT AGC AGC AGC GAT  1920
Ser Phe Asn Gln Thr Gly Thr Ala Thr Gly Arg Leu Ser Ser Ser Asp
625             630             635             640

CCC AAT CTT CAG AAC CTC CCG ACG AAA AGT GAA GAG GGA AAA GAA ATC  1968
Pro Asn Leu Gln Asn Leu Pro Thr Lys Ser Glu Glu Gly Lys Glu Ile
                645             650             655

AGG AAA GCG ATA GTT CCT CAG GAT CCA AAC TGG TGG ATC GTC AGT GCC  2016
Arg Lys Ala Ile Val Pro Gln Asp Pro Asn Trp Trp Ile Val Ser Ala
            660             665             670

GAC TAC TCC CAA ATA GAA CTG AGG ATC CTC GCC CAT CTC AGT GGT GAT  2064
Asp Tyr Ser Gln Ile Glu Leu Arg Ile Leu Ala His Leu Ser Gly Asp
        675             680             685

GAG AAT CTT TTG AGG GCA TTC GAA GAG GGC ATC GAC GTC CAC ACT CTA  2112
Glu Asn Leu Leu Arg Ala Phe Glu Glu Gly Ile Asp Val His Thr Leu
690             695             700

ACA GCT TCC AGA ATA TTC AAC GTG AAA CCC GAA GAA GTA ACC GAA GAA  2160
Thr Ala Ser Arg Ile Phe Asn Val Lys Pro Glu Glu Val Thr Glu Glu
705             710             715             720

ATG CGC CGC GCT GGT AAA ATG GTT AAT TTT TCC ATC ATA TAC GGT GTA  2208
Met Arg Arg Ala Gly Lys Met Val Asn Phe Ser Ile Ile Tyr Gly Val
                725             730             735

ACA CCT TAC GGT CTG TCT GTG AGG CTT GGA GTA CCT GTG AAA GAA GCA  2256
Thr Pro Tyr Gly Leu Ser Val Arg Leu Gly Val Pro Val Lys Glu Ala
            740             745             750

GAA AAG ATG ATC GTC AAC TAC TTC GTC CTC TAC CCA AAG GTG CGC GAT  2304
Glu Lys Met Ile Val Asn Tyr Phe Val Leu Tyr Pro Lys Val Arg Asp
        755             760             765

TAC ATT CAG AGG GTC GTA TCG GAA GCG AAA GAA AAG GGC TAT GTT AGA  2352
Tyr Ile Gln Arg Val Val Ser Glu Ala Lys Glu Lys Gly Tyr Val Arg
770             775             780

ACG CTG TTT GGA AGA AAA AGA GAC ATA CCA CAG CTC ATG GCC CGG GAC  2400
Thr Leu Phe Gly Arg Lys Arg Asp Ile Pro Gln Leu Met Ala Arg Asp
785             790             795             800

AGG AAC ACA CAG GCT GAA GGA GAA CGA ATT GCC ATA AAC ACT CCC ATA  2448
Arg Asn Thr Gln Ala Glu Gly Glu Arg Ile Ala Ile Asn Thr Pro Ile
                805             810             815

CAG GGT ACA GCA GCG GAT ATA ATA AAG CTG GCT ATG ATA GAA ATA GAC  2496
Gln Gly Thr Ala Ala Asp Ile Ile Lys Leu Ala Met Ile Glu Ile Asp
            820             825             830

AGG GAA CTG AAA GAA AGA AAA ATG AGA TCG AAG ATG ATC ATA CAG GTC  2544
Arg Glu Leu Lys Glu Arg Lys Met Arg Ser Lys Met Ile Ile Gln Val
        835             840             845

CAC GAC GAA CTG GTT TTT GAA GTG CCC AAT GAG GAA AAG GAC GCG CTC  2592
His Asp Glu Leu Val Phe Glu Val Pro Asn Glu Glu Lys Asp Ala Leu
850             855             860
```

```
GTC GAG CTG GTG AAA GAC AGA ATG ACG AAT GTG GTA AAG CTT TCA GTG   2640
Val Glu Leu Val Lys Asp Arg Met Thr Asn Val Val Lys Leu Ser Val
865                 870                 875                 880

CCG CTC GAA GTG GAT GTA ACC ATC GGC AAA ACA TGG TCG TGA           2682
Pro Leu Glu Val Asp Val Thr Ile Gly Lys Thr Trp Ser
                885                 890
```

( 2 ) INFORMATION FOR SEQ ID NO: 2:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 2:

CGAGATCTGG NTA Y GTWGAA AC                    22

( 2 ) INFORMATION FOR SEQ ID NO: 3:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 3:

CGAGATCTGG NTA Y GTWGAG AC                    22

( 2 ) INFORMATION FOR SEQ ID NO: 4:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 4:

CGAGATCTGG NTA Y GTSGAA AC                    22

( 2 ) INFORMATION FOR SEQ ID NO: 5:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 5:

CGAGATCTGG NTA Y GTSGAG AC                    22

( 2 ) INFORMATION FOR SEQ ID NO: 6:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 6:

CGGAATTCRT CRTGWACCTG                    20

( 2 ) INFORMATION FOR SEQ ID NO: 7:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 7:

CGGAATTCRT CRTGWACTTG                    20

( 2 ) INFORMATION FOR SEQ ID NO: 8:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 8:

CGGAATTCRT CRTGSACCTG                    20

( 2 ) INFORMATION FOR SEQ ID NO: 9:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 9:

CGGAATTCRT CRTGSACTTG                    20

( 2 ) INFORMATION FOR SEQ ID NO: 10:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 10:

CGAGATCTAC NGCNACWGG                     19

( 2 ) INFORMATION FOR SEQ ID NO: 11:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 11:

CGAGATCTAC NGCNACSGG                     19

( 2 ) INFORMATION FOR SEQ ID NO: 12:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 12:

ACAGCAGCKG ATATAATAAA G         21

( 2 ) INFORMATION FOR SEQ ID NO: 13:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 13:

GCCATGAGCT GTGGTATGTC TC         22

( 2 ) INFORMATION FOR SEQ ID NO: 14:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 14:

TACGTTCCCG GGCCTTGTAC         20

( 2 ) INFORMATION FOR SEQ ID NO: 15:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 15:

AGGAGGTGAT CCAACCGCA         19

( 2 ) INFORMATION FOR SEQ ID NO: 16:

( i ) SEQUENCE CHARACTERISTICS:
        ( A ) LENGTH: 48 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 16:

CCATCAAAAA GAAATAGTCT AGCCATATGT GTTCCTGTG TGAAATTG         48

( 2 ) INFORMATION FOR SEQ ID NO: 17:

( i ) SEQUENCE CHARACTERISTICS:
        ( A ) LENGTH: 18 bases
        ( B ) TYPE: nucleic acid (C) STRANDEDNESS: single
(D) TOPOLOGY: linear (ii) MOLECULE TYPE: Other Nucleic Acid (xi) SEQUENCE DESCRIPTION: SEQ ID NO: 17:

AAACACATAT GGCTAGAC 18

(2) INFORMATION FOR SEQ ID NO: 18:

(i) SEQUENCE CHARACTERISTICS:
(A) LENGTH: 48 bases
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO: 18:

CCATCAAAAA GAAATAGTCT AGCCATGGTT GTTTCCTGTG TGAAATTG 48

(2) INFORMATION FOR SEQ ID NO: 19:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO: 19:

AAACAACCAT GGCTAGAC 18

(2) INFORMATION FOR SEQ ID NO: 20:

(i) SEQUENCE CHARACTERISTICS:
(A) LENGTH: 44 bases
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO: 20:

GCAAAACATG GTCGTGATAT CGGATCCGGA GGTGTTATCT GTGG 44

(2) INFORMATION FOR SEQ ID NO: 21:

(i) SEQUENCE CHARACTERISTICS:
(A) LENGTH: 17 bases
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO: 21:

CCGATATCAC GACCATG 17

(2) INFORMATION FOR SEQ ID NO: 22:

(i) SEQUENCE CHARACTERISTICS:
(A) LENGTH: 28 bases
(B) TYPE: nucleic acid
(C) STRANDEDNESS: single
(D) TOPOLOGY: linear (ii) MOLECULE TYPE: Other Nucleic Acid ( x i ) SEQUENCE DESCRIPTION: SEQ ID NO: 22:

CCGGAAGAAG GAGATATACA TATGAGCT                                         28

( 2 ) INFORMATION FOR SEQ ID NO: 23:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 23:

CATATGTATA TCTCCTTCTT                                                  20

( 2 ) INFORMATION FOR SEQ ID NO: 24:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 24:

CCGGAGGAGA AAACATATGA GCT                                              23

( 2 ) INFORMATION FOR SEQ ID NO: 25:

( i ) SEQUENCE CHARACTERISTICS:
        ( A ) LENGTH: 15 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 25:

CATATGTTTT CTCCT                                                       15

( 2 ) INFORMATION FOR SEQ ID NO: 26:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 26:

CCGGAAGAAG GAGAAAATAC CATGGGCCCG GTAC                                  34

( 2 ) INFORMATION FOR SEQ ID NO: 27:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 27:

CGGGCCCATG GTATTTCTC CTTCTT                                            26

( 2 ) INFORMATION FOR SEQ ID NO: 28:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 28:

CCGGAGGAGA AAATCCATGG GCCCGGTAC         29

( 2 ) INFORMATION FOR SEQ ID NO: 29:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 29:

CGGGCCCATG GATTTCTCC T         21

( 2 ) INFORMATION FOR SEQ ID NO: 30:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 30:

GATAAAGGCA TGCTTCAGCT TGTGAACG         28

( 2 ) INFORMATION FOR SEQ ID NO: 31:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 31:

TGTACTTCTC TAGAAGCTGA ACAGCAG         27

( 2 ) INFORMATION FOR SEQ ID NO: 32:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 32:

CTGAAGCATG TCTTTGTCAC CGGTTACTAT GAATAT         36

( 2 ) INFORMATION FOR SEQ ID NO: 33:

( i ) SEQUENCE CHARACTERISTICS:
  ( A ) LENGTH: 18 bases
  ( B ) TYPE: nucleic acid
  ( C ) STRANDEDNESS: single
  ( D ) TOPOLOGY: linear ( i i ) MOLECULE TYPE: Other Nucleic Acid ( x i ) SEQUENCE DESCRIPTION: SEQ ID NO: 33:

TAGTAACCGG TGACAAAG        18

( 2 ) INFORMATION FOR SEQ ID NO: 34:

( i ) SEQUENCE CHARACTERISTICS:
    ( A ) LENGTH: 31 bases
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO: 34:

CTATGCCATG GATAGATCGC TTTCTACTTC C        31

( 2 ) INFORMATION FOR SEQ ID NO: 35:

( i ) SEQUENCE CHARACTERISTICS:
    ( A ) LENGTH: 31 bases
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO: 35:

CAAGCCCATG GAAACTTACA AGGCTCAAAG A        31

( 2 ) INFORMATION FOR SEQ ID NO: 36:

( i ) SEQUENCE CHARACTERISTICS:
    ( A ) LENGTH: 60 bases
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO: 36:

TCAGCTTAAG ACTTCGAAAT TAATACGACT CACTATAGGG AGACCACAAC GGTTCCCTC        60

( 2 ) INFORMATION FOR SEQ ID NO: 37:

( i ) SEQUENCE CHARACTERISTICS:
    ( A ) LENGTH: 62 bases
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO: 37:

TCGACCATGG GTATATCTCC TTCTTAAAGT TAAACAAAAT TATTTCTAGA GGGAAACCGT        60
TG        62

( 2 ) INFORMATION FOR SEQ ID NO: 38:

( i ) SEQUENCE CHARACTERISTICS:
    ( A ) LENGTH: 42 bases
    ( B ) TYPE: nucleic acid ( C ) STRANDEDNESS: single
( D ) TOPOLOGY: linear ( i i ) MOLECULE TYPE: Other Nucleic Acid ( x i ) SEQUENCE DESCRIPTION: SEQ ID NO: 38:

TCAGTCCGGA TAAACAAAAT TATTTCTAGA GGGAAACCGT TG  42

( 2 ) INFORMATION FOR SEQ ID NO: 39:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 39:

TCCGGACTTT AAGAAGGAGA TATAC  25

( 2 ) INFORMATION FOR SEQ ID NO: 40:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 40:

AATAGTCTAG CCATCAGAAA GTCTCCTGTG C  31

( 2 ) INFORMATION FOR SEQ ID NO: 41:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 41:

AGACTTTCTG ATGGCTAGAC TATTTCTT  28

( 2 ) INFORMATION FOR SEQ ID NO: 42:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 42:

CTGAATCAGG AGACCCGGGG TCTTTGGTC  29

( 2 ) INFORMATION FOR SEQ ID NO: 43:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO: 43:

CGGGGATCCA AAAGCCATTG ACTCAGCAAG G   31

( 2 ) INFORMATION FOR SEQ ID NO: 44:

( i ) SEQUENCE CHARACTERISTICS:
    ( A ) LENGTH: 30 bases
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO: 44:

GGGGGTCGAC GCATGCGAGG AAAATAGACG   30

( 2 ) INFORMATION FOR SEQ ID NO: 45:

( i ) SEQUENCE CHARACTERISTICS:
    ( A ) LENGTH: 25 bases
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO: 45:

GGCGTACCTT TGTCTCACGG GCAAC   25

( 2 ) INFORMATION FOR SEQ ID NO: 46:

( i ) SEQUENCE CHARACTERISTICS:
    ( A ) LENGTH: 74 bases
    ( B ) TYPE: nucleic acid
    ( C ) STRANDEDNESS: single
    ( D ) TOPOLOGY: linear ( i i ) MOLECULE TYPE: Other Nucleic Acid ( x i ) SEQUENCE DESCRIPTION: SEQ ID NO: 46:

CTTTAAGAAG GAGATATACA TATGGCTAGC ATGACTGGTG GACAGCAAAT GCATGCACAG   60

GAGACTTTCT GATG   74